(12) United States Patent
Begley et al.

(10) Patent No.: US 7,968,215 B2
(45) Date of Patent: Jun. 28, 2011

(54) OLED DEVICE WITH CYCLOBUTENE ELECTRON INJECTION MATERIALS

(75) Inventors: William J. Begley, Webster, NY (US); Natasha Andrievsky, Webster, NY (US)

(73) Assignee: Global OLED Technology LLC, Wilmington, DE (US)

( * ) Notice: Subject to any disclaimer, the term of this patent is extended or adjusted under 35 U.S.C. 154(b) by 287 days.

(21) Appl. No.: 12/330,547

(22) Filed: Dec. 9, 2008

(65) Prior Publication Data

US 2010/0141122 A1 Jun. 10, 2010

(51) Int. Cl.
- *H01L 51/54* (2006.01)
- *C07D 401/02* (2006.01)
- *C07D 471/04* (2006.01)
- *C07D 403/02* (2006.01)
- *C07D 213/16* (2006.01)
- *C07D 401/14* (2006.01)
- *C07D 409/14* (2006.01)

(52) U.S. Cl. ........ 428/690; 428/917; 313/504; 313/506; 544/296; 546/255; 546/88; 546/350; 546/165; 546/256

(58) Field of Classification Search .................. None
See application file for complete search history.

(56) References Cited

U.S. PATENT DOCUMENTS

| | | | |
|---|---|---|---|
| 3,172,862 A | 3/1965 | Gurnee et al. |
| 3,173,050 A | 3/1965 | Gurnee |
| 3,180,730 A | 4/1965 | Klupfel et al. |
| 3,567,450 A | 3/1971 | Brantly et al. |
| 3,658,520 A | 4/1972 | Brantly et al. |
| 3,710,167 A | 1/1973 | Dresner |
| 4,356,429 A | 10/1982 | Tang |
| 4,539,507 A | 9/1985 | Vanslyke et al. |
| 4,720,432 A | 1/1988 | Vanslyke et al. |
| 4,768,292 A | 9/1988 | Manzei et al. |
| 4,769,292 A | 9/1988 | Tang et al. |
| 4,885,211 A | 12/1989 | Tang et al. |
| 4,885,221 A | 12/1989 | Tsuneeda et al. |
| 5,059,861 A | 10/1991 | Littman et al. |
| 5,059,862 A | 10/1991 | VanSlyke et al. |
| 5,061,569 A | 10/1991 | VanSlyke et al. |
| 5,077,142 A | 12/1991 | Sakon et al. |
| 5,121,029 A | 6/1992 | Hosokawa et al. |
| 5,141,671 A | 8/1992 | Bryan et al. |

(Continued)

FOREIGN PATENT DOCUMENTS

EP   681019   11/1995

(Continued)

OTHER PUBLICATIONS

"Double Injection Electroluminescence in Anthracene", RCA Review, 30, 322, (1969).

(Continued)

*Primary Examiner* — Dawn L Garrett
(74) *Attorney, Agent, or Firm* — McKenna Long & Aldridge LLP

(57) ABSTRACT

An OLED device including a cathode, an anode, and having therebetween a light-emitting layer and further comprising a first layer between the light-emitting layer and the cathode containing a cyclobutene compound comprising a cyclobutene nucleus substituted in the 1-position with a five- or six-membered heteroaromatic ring group containing at least one trivalent nitrogen atom; substituted in the 2-position with an aromatic ring group; and substituted with a first methylene group in the 3-position and a second methylene group in the 4-position, provided said first and second methylene groups are further disubstituted in the 1',1'-positions and the 1",1"-positions with independently selected aromatic groups.

20 Claims, 2 Drawing Sheets

U.S. PATENT DOCUMENTS

| | | | |
|---|---|---|---|
| 5,150,006 A | 9/1992 | Van Slyke et al. |
| 5,151,629 A | 9/1992 | Van Slyke et al. |
| 5,247,190 A | 9/1993 | Friend et al. |
| 5,276,380 A | 1/1994 | Tang |
| 5,294,870 A | 3/1994 | Tang et al. |
| 5,405,709 A | 4/1995 | Littman et al. |
| 5,409,783 A | 4/1995 | Tang et al. |
| 5,484,922 A | 1/1996 | Moore et al. |
| 5,552,678 A | 9/1996 | Tang et al. |
| 5,554,450 A | 9/1996 | Shi et al. |
| 5,593,788 A | 1/1997 | Shi et al. |
| 5,608,287 A | 3/1997 | Hung et al. |
| 5,645,948 A | 7/1997 | Shi et al. |
| 5,677,572 A | 10/1997 | Hung et al. |
| 5,683,823 A | 11/1997 | Shi et al. |
| 5,688,551 A | 11/1997 | Littman et al. |
| 5,703,436 A | 12/1997 | Forrest et al. |
| 5,714,838 A | 2/1998 | Haight et al. |
| 5,739,545 A | 4/1998 | Guha et al. |
| 5,755,999 A | 5/1998 | Shi et al. |
| 5,766,779 A | 6/1998 | Shi et al. |
| 5,776,622 A | 7/1998 | Hung et al. |
| 5,776,623 A | 7/1998 | Hung et al. |
| 5,837,391 A | 11/1998 | Utsugi |
| 5,851,709 A | 12/1998 | Grande et al. |
| 5,908,581 A | 6/1999 | Chen et al. |
| 5,927,247 A | 7/1999 | Tanaka |
| 5,928,802 A | 7/1999 | Shi et al. |
| 5,929,194 A | 7/1999 | Woo et al. |
| 5,935,720 A | 8/1999 | Chen et al. |
| 5,935,721 A | 8/1999 | Shi et al. |
| 5,969,474 A | 10/1999 | Arai |
| 5,981,306 A | 11/1999 | Burrows et al. |
| 6,020,078 A | 2/2000 | Chen et al. |
| 6,066,357 A | 5/2000 | Tang et al. |
| 6,097,147 A | 8/2000 | Baldo et al. |
| 6,137,223 A | 10/2000 | Hung et al. |
| 6,140,763 A | 10/2000 | Hung et al. |
| 6,172,459 B1 | 1/2001 | Hung et al. |
| 6,208,075 B1 | 3/2001 | Hung et al. |
| 6,208,077 B1 | 3/2001 | Hung |
| 6,226,890 B1 | 5/2001 | Boroson et al. |
| 6,237,529 B1 | 5/2001 | Spahn |
| 6,278,236 B1 | 8/2001 | Madathil et al. |
| 6,284,393 B1 | 9/2001 | Hosokawa et al. |
| 6,337,492 B1 | 1/2002 | Jones et al. |
| 6,396,209 B1 | 5/2002 | Kido et al. |
| 6,423,429 B2 | 7/2002 | Kido et al. |
| 6,468,676 B1 | 10/2002 | Ueda et al. |
| 6,509,109 B1 | 1/2003 | Nakamura |
| 6,613,454 B2 | 9/2003 | Ara et al. |
| 6,661,023 B2 | 12/2003 | Hoag et al. |
| 6,689,493 B2 | 2/2004 | Motomatsu et al. |
| 6,720,092 B2 | 4/2004 | Hatwar |
| 6,720,573 B2 | 4/2004 | Son et al. |
| 6,773,832 B2 | 8/2004 | Sotoyama et al. |
| 6,803,120 B2 | 10/2004 | Fukuoka et al. |
| 6,824,895 B1 | 11/2004 | Sowinski et al. |
| 6,866,947 B1 | 3/2005 | Fukuoka et al. |
| 6,927,537 B2 | 8/2005 | Takahashi |
| 6,936,961 B2 | 8/2005 | Liao et al. |
| 7,165,340 B2 | 1/2007 | Long et al. |
| 7,175,922 B2 | 2/2007 | Jarikov |
| 7,183,010 B2 | 2/2007 | Jarikov |
| 7,232,588 B2 | 6/2007 | Long et al. |
| 7,238,389 B2 | 7/2007 | Long et al. |
| 7,288,285 B2 | 10/2007 | Long et al. |
| 7,288,286 B2 | 10/2007 | Long et al. |
| 7,625,601 B2 | 12/2009 | Long |
| 7,767,317 B2 | 8/2010 | Begley et al. |
| 2002/0022151 A1 | 2/2002 | Ishikawa et al. |
| 2002/0086180 A1 | 7/2002 | Seo et al. |
| 2002/0168544 A1 | 11/2002 | Fukuoka et al. |
| 2003/0044643 A1 | 3/2003 | Arakane et al. |
| 2003/0068528 A1 | 4/2003 | Thompson et al. |
| 2004/0113547 A1 | 6/2004 | Son et al. |
| 2004/0207318 A1 | 10/2004 | Lee et al. |
| 2004/0255857 A1 | 12/2004 | Chow et al. |
| 2005/0067955 A1 | 3/2005 | Cho et al. |
| 2005/0097955 A1 | 5/2005 | Berg et al. |
| 2005/0244676 A1 | 11/2005 | Arakane et al. |
| 2005/0271889 A1 | 12/2005 | Dolinar |
| 2005/0271899 A1 | 12/2005 | Brown et al. |
| 2006/0097227 A1 | 5/2006 | Okajima et al. |
| 2006/0134460 A1 | 6/2006 | Kondakova et al. |
| 2006/0141287 A1 | 6/2006 | Klubek et al. |
| 2006/0177576 A1 | 8/2006 | Long et al. |
| 2006/0238110 A1 | 10/2006 | Shirai et al. |
| 2006/0246315 A1 | 11/2006 | Begley et al. |
| 2006/0257684 A1 | 11/2006 | Arakane et al. |
| 2006/0286405 A1 | 12/2006 | Begley et al. |
| 2007/0063189 A1 | 3/2007 | Schwalm et al. |
| 2007/0069198 A1 | 3/2007 | Dotz et al. |
| 2007/0092756 A1 | 4/2007 | Begley et al. |
| 2007/0092759 A1 | 4/2007 | Begley et al. |
| 2007/0122657 A1 | 5/2007 | Klubek et al. |
| 2007/0149815 A1 | 6/2007 | Takada et al. |
| 2007/0207347 A1 | 9/2007 | Begley et al. |
| 2007/0252516 A1 | 11/2007 | Kondakova et al. |
| 2008/0007160 A1 | 1/2008 | Sado et al. |

FOREIGN PATENT DOCUMENTS

| | | |
|---|---|---|
| EP | 0 732 868 | 9/1996 |
| EP | 0 891 121 | 1/1999 |
| EP | 1 009 041 | 6/2000 |
| EP | 1 029 909 A1 | 8/2000 |
| EP | 1 076 368 | 2/2001 |
| EP | 1 097 980 | 5/2001 |
| EP | 1 718 124 | 11/2006 |
| EP | 1 719 748 | 11/2006 |
| JP | 8-333569 | 12/1996 |
| JP | 09-13026 | 1/1997 |
| JP | 2000-53957 | 2/2000 |
| JP | 2002-069044 | 3/2002 |
| JP | 200409144 | 1/2004 |
| JP | 2004-091444 | 3/2004 |
| JP | 2005-320286 | 11/2005 |
| WO | WO 98/55561 | 12/1998 |
| WO | WO 99/63023 | 12/1999 |
| WO | WO 00/18851 | 4/2000 |
| WO | WO 00/57676 | 9/2000 |
| WO | WO 00/70655 | 11/2000 |
| WO | WO 01/41512 | 6/2001 |
| WO | WO 01/93642 | 12/2001 |
| WO | WO 2004/026870 | 4/2004 |
| WO | WO 2005/033051 | 4/2005 |
| WO | WO 2006/138075 | 12/2006 |
| WO | WO 2007/039344 | 4/2007 |
| WO | WO 2007/126112 | 11/2007 |

OTHER PUBLICATIONS

C. Tang et al. "Electroluminescence of Doped Organic Thin Films", Journal of Applied Physics, 65, 3610 (1989).

Nonoyama, "Benzo[h]quinolin-10-yl-N Iridium (III) Complexes", Bulletin of the Chemical Society of Japan, vol. 47(3), pp. 767-768, 1974.

Johnson et al., "Luminescent Iridium(I), Rhodium(I), and Platinum(II) Dithiolate Complexes", Journal of American Chemical Society, vol. 105, pp. 1795-1802, 1983.

Wrighton et al., The Nature of the Lowest Excited State in Tricarbonylchloro-1,10-phenanthrolinerhenium(I) and Related Complexes, Journal of the American Chemical Society, vol. 96, No. 4, pp. 998-1003, 1974.

Stufkens, Comments Inorg. Chem., 13, 359 (1992).

Yam, "Luminescent carbon-rich rhenium(I) complexes", Chem. Commun. pp. 789-796, 2001.

Ma et al., "Electroluminescence from triplet metal-ligand charge-transfer excited state of transition metal complexes", Synthetic Metals 94, pp. 245-248, 1998.

Kido et al., "Electroluminescence in a Terbium Complex", Chem. Lett. pp. 657-660, 1990.

Kido et al., "Organic electroluminescent devices using lanthanide complexes", J. Alloys and Compounds 192, pp. 30-33, 1993.

Kido et al., White-Light-Emitting Organic Electroluminescent Device Using Lanthanide Complexes, Jpn. J. Appl. Phys., vol. 35, pp. L394-L396, 1996.

Kido et al., "Bright red light-emitting organic electroluminescent devices having a europium complex as an emitter", Appl. Phys. Lett., 65 (17), pp. 2124-2126, 1994.

Chen, Shi, and Tang, "Recent Developments in Molecular Organic Electroluminescent Materials," Macromol. Symp. 125, 1-48 (1997).

Hung et al., "Recent progress of molecular organic electroluminescent materials and devices", Materials Science and Engineering R39, pp. 143-222, 2002.

Marappan Velusamy et al., Dalton Trans., 3025-3034 (2007).

R. Tseng et al., "Highly Efficient 7,8,10-triphenylfluoranthene-doped blue organic light-emitting diodoes for display application", Applied Physics Letters, vol. 88, No. 9, pp. 093512-1 to 093512-3, 2006.

Rule et al., "Acenaphthenone and Acenaphthenequinone", Journal of the Chemical Society, pp. 1761-1763, 1937.

Dong et al, Switching the light emission of (4-biphenylyl)phenyldibenzofulvene by morphological modulation: crystallization-induced emission enhancement, Chem Comm, 3255-3257 (2007).

Iyoda et al, A Novel One-step Nickel-Mediated Synthetis of C6Ar6 Conjugated Hydrocarbons, Highly Substituted and Over Crowded Fulvenes and 3,4-dimethylenecyclobutenes, Chem. Lett. 149-152 (1988).

OLED DEVICE WITH CYCLOBUTENE ELECTRON INJECTION MATERIALS

CROSS-REFERENCE TO RELATED APPLICATIONS

Reference is made to commonly-assigned U.S. patent application Ser. No. 11/924,629 filed Oct. 26, 2007, entitled OLED DEVICE WITH CERTAIN FLUORANTHENE LIGHT-EMITTING DOPANTS, by Begley et al, U.S. patent application Ser. No. 11/924,624 filed Oct. 26, 2007, entitled OLED DEVICE WITH CERTAIN FLUORANTHENE HOSTS by Begley et al, U.S. patent application Ser. No. 11/924,631 filed Oct. 26, 2007, entitled OLED DEVICE WITH FLUORANTHENE ELECTRON TRANSPORT MATERIALS by Begley et al, and U.S. patent application Ser. No. 12/266,802 filed Nov. 7, 2008 entitled ELECTROLUMINESCENT DEVICE CONTAINING A FLOURANTHENE DERIVATIVE by Begley et al and U.S. patent application Ser. No. 12/269,066 filed Nov. 12, 2008, entitled OLED DEVICE WITH FLUORANTHENE ELECTRON INJECTING MATERIALS by Begley et al, the disclosures of which are incorporated herein by reference.

FIELD OF THE INVENTION

This invention relates to a specific type of cyclobutene compound and to an organic light-emitting diode (OLED) electroluminescent (EL) device having a light-emitting layer and an electron-transporting or electron-injecting layer including the cyclobutene compound.

BACKGROUND OF THE INVENTION

While organic electroluminescent (EL) devices have been known for over two decades, their performance limitations have represented a barrier to many desirable applications. In simplest form, an organic EL device includes an anode for hole injection, a cathode for electron injection, and an organic medium sandwiched between these electrodes to support charge recombination that yields emission of light. These devices are also commonly referred to as organic light-emitting diodes, or OLEDs. Representative of earlier organic EL devices are Gurnee et al. U.S. Pat. No. 3,172,862, Gurnee U.S. Pat. No. 3,173,050; Dresner, "Double Injection Electroluminescence in Anthracene", RCA Review, 30, 322, (1969); and Dresner U.S. Pat. No. 3,710,167. The organic layers in these devices, usually composed of a polycyclic aromatic hydrocarbon, were very thick (much greater than 1 μm). Consequently, operating voltages were very high, often greater than 100V.

More recent organic EL devices include an organic EL element consisting of extremely thin layers (e.g. <1.0 μm) between the anode and the cathode. Herein, the term "organic EL element" encompasses the layers between the anode and cathode. Reducing the thickness lowered the resistance of the organic layers and has enabled devices that operate at much lower voltage. In a basic two-layer EL device structure, described first in U.S. Pat. No. 4,356,429, one organic layer of the EL element adjacent to the anode is specifically chosen to transport holes, and therefore is referred to as the hole-transporting layer, and the other organic layer is specifically chosen to transport electrons and is referred to as the electron-transporting layer. Recombination of the injected holes and electrons within the organic EL element results in efficient electroluminescence.

There have also been proposed three-layer organic EL devices that contain an organic light-emitting layer (LEL) between the hole-transporting layer and electron-transporting layer, such as that disclosed by C. Tang et al. (J. Applied Physics, Vol. 65, 3610 (1989)). The light-emitting layer commonly consists of a host material doped with a guest material, otherwise known as a dopant. Still further, there has been proposed in U.S. Pat. No. 4,769,292 a four-layer EL element comprising a hole-injecting layer (HIL), a hole-transporting layer (HTL), a light-emitting layer (LEL) and an electron-transporting/injecting layer (ETL). These structures have resulted in improved device efficiency.

EL devices in recent years have expanded to include not only single color emitting devices, such as red, green and blue, but also white-devices, devices that emit white light. Efficient white light producing OLED devices are highly desirable in the industry and are considered as a low cost alternative for several applications such as paper-thin light sources, backlights in LCD displays, automotive dome lights, and office lighting. White light producing OLED devices should be bright, efficient, and generally have Commission International d'Eclairage (CIE) chromaticity coordinates of about (0.33, 0.33). In any event, in accordance with this disclosure, white light is that light which is perceived by a user as having a white color.

Since the early inventions, further improvements in device materials have resulted in improved performance in attributes such as color, stability, luminance efficiency and manufacturability, e.g., as disclosed in U.S. Pat. Nos. 5,061,569; 5,409,783; 5,554,450; 5,593,788; 5,683,823; 5,908,581; 5,928,802; 6,020,078, and 6,208,077, amongst others.

Notwithstanding all of these developments, there are continuing needs for organic EL device components, such as electron-transporting materials and electron-injecting materials, which will provide even lower device drive voltages and hence lower power consumption, while maintaining high luminance efficiencies and long lifetimes combined with high color purity.

A useful class of electron-transporting materials is that derived from metal chelated oxinoid compounds including chelates of oxine itself, also commonly referred to as 8-quinolinol or 8-hydroxyquinoline. Tris(8-quinolinolato)aluminum (III), also known as Alq or $Alq_3$, and other metal and non-metal oxine chelates are well known in the art as electron-transporting materials. Tang et al., in U.S. Pat. No. 4,769,292 and VanSlyke et al., in U.S. Pat. No. 4,539,507 lower the drive voltage of the EL devices by teaching the use of Alq as an electron transport material in the luminescent layer or luminescent zone. Baldo et al., in U.S. Pat. No. 6,097,147 and Hung et al., in U.S. Pat. No. 6,172,459 teach the use of an organic electron-transporting layer adjacent to the cathode so that when electrons are injected from the cathode into the electron-transporting layer, the electrons traverse both the electron-transporting layer and the light-emitting layer.

The use of substituted fluoranthenes in an electron-transporting layer is also known, examples include devices described in U.S. Patent Application Publication Nos. 2008/0007160, US20070252516, 2006/0257684, 2006/0097227, and JP 200409144, the disclosures of which are incorporated herein by reference.

Examples of electron-injecting layers include those described in U.S. Pat. Nos. 5,608,287; 5,776,622; 5,776,623; 6,137,223, and 6,140,763, the disclosures of which are incorporated herein by reference. An electron-injecting layer generally consists of a material having a work function less than 4.0 eV. The definition of work function can be found in CRC Handbook of Chemistry and Physics, 70th Edition, 1989-1990, CRC Press Inc., page F-132 and a list of the work functions for various metals can be found on pages E-93 and E-94. Typical examples of such metals include Li, Na, K, Be, Mg, Ca, Sr, Ba, Y, La, Sm, Gd, Yb. A thin-film containing low work-function alkali metals or alkaline earth metals, such as Li, Cs, Ca, Mg can be employed for electron-injection. In addition, an organic material doped with these low work-function metals can also be used effectively as the electron-injecting layer. Examples are Li- or Cs-doped Alq.

U.S. Pat. No. 6,509,109 and U.S. Patent Application Publication No. 2003/0044643, the disclosures of which are incorporated herein by reference, describe an organic electroluminescent device wherein the electron injection region contains a nitrogen-free aromatic compound as a host material and a reducing dopant, such as an alkali metal compound. U.S. Pat. No. 6,396,209, the disclosure of which is incorporated herein by reference, describes an electron injection layer of an electron-transporting organic compound and an organic metal complex compound containing at least one alkali metal ion, alkaline earth metal ion or rare earth metal ion. Additional examples of organic lithium compounds in an electron-injection layer of an EL device include U.S. Patent Application Publication Nos. 2006/0286405, 2002/0086180, 2004/0207318, U.S. Pat. Nos. 6,396,209; 6,468,676, JP 2000053957, and WO 9963023 the disclosures of which are incorporated herein by reference.

U.S. Pat. No. 5,077,142, the disclosure of which is incorporated herein by reference, broadly describes a large number of compounds that can be useful for OLED devices. Among the compounds disclosed are certain cyclobutene derivatives. M. Tyoda et al., *Chem, Lett.*, 149-52 (1988) and Y. Dong, *Chem. Comm.*, 3255-3257 (2007), describe the preparation of 1,2-diphenyl-3,4-bis(diphenylmethylene)-1-cyclobutene and related compounds.

Notwithstanding all these developments, there remains a need to develop novel compounds that improve efficiency and reduce drive voltage of OLED devices, as well as to provide embodiments with other improved features.

SUMMARY OF THE INVENTION

An OLED device including a cathode, an anode, and having therebetween a light-emitting layer, further includes, between the cathode and the light emitting layer, a first layer containing a cyclobutene compound. The cyclobutene compound includes a cyclobutene nucleus substituted in the 1-position with a five- or six-membered heteroaromatic ring group containing at least one trivalent nitrogen atom; substituted in the 2-position with an aromatic ring group; substituted with a first methylene group in the 3-position and a second methylene group in the 4-position, provided the first and second methylene groups are further disubstituted in the 1',1'-positions and the 1",1"-positions with independently selected aromatic groups.

In a second embodiment, the OLED device includes an alkali metal or alkali metal compound wherein the alkali metal or alkali metal compound is present in the first layer or in a second layer located between the cathode and the first layer.

In a third embodiment, the OLED device includes a polycyclic aromatic hydrocarbon compound which is present in the first layer, in addition to the cyclobutene compound, or in a third layer located between the first layer and the light-emitting layer.

Devices of the invention provide improvement in features such as efficiency and drive voltage.

DETAILED DESCRIPTION OF THE INVENTION

Figure 1:
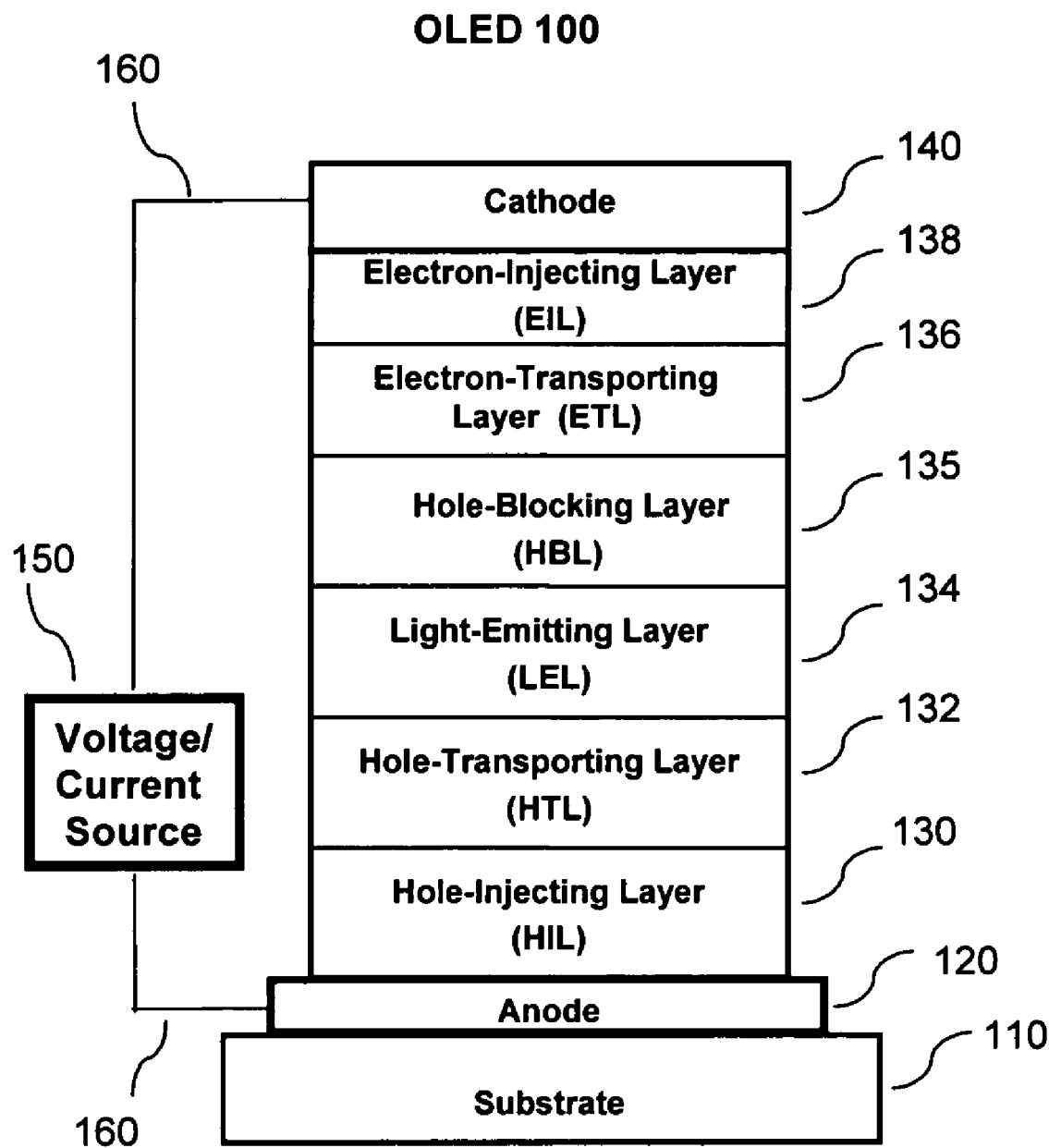
FIG. 1 shows a schematic cross-sectional view of one embodiment of the OLED device of the present invention. It will be understood that FIG. 1 is not to scale since the individual layers are too thin and the thickness differences of various layers are too great to permit depiction to scale.

The invention is generally as described above. An OLED device of the invention is a multilayer electroluminescent device including a cathode, an anode, light-emitting layer(s) (LEL), electron-transporting layer(s) (ETL) and electron-injecting layer(s) (EIL) and optionally additional layers such as hole-injecting layer(s), hole-transporting layer(s), exciton-blocking layer(s), spacer layer(s), connecting layer(s) and hole-blocking layer(s).

A first layer between the light-emitting layer and the cathode includes a cyclobutene compound. The cyclobutene compound facilitates the transport of electrons from the cathode to the light-emitting layer. For example, the first layer can be an electron-injecting layer. The thickness of the electron-injecting layer is often in the range of 0.1 nm to 50 nm, but preferably 0.4 nm to 10 nm, and more preferable from 1 nm to 8 nm. In one embodiment, the thickness of the first layer is 10 nm or less or even 5 nm or less. The thickness of the organic layers can be controlled and measured during device fabrication using calibrated thickness monitors such as, for example, an INFICON IC/5 Deposition Controller made by Inficon Inc., Syracuse, N.Y. The electron-injecting layer can be subdivided further into two or more sub-layers, for example, it can be divided into a first (EIL1) and a second (EIL2) injection layer and it can be further divided.

The cyclobutene compound is also useful in electron-transporting layers. The electron-transporting layer is present between the light-emitting layer and the cathode and often has a thickness of 1-100 nm, or 5-50 nm, or more frequently 10-40 nm. When an electron-injection layer is present, the electron-transporting layer (ETL) is located between the electron-injecting layer and the light emitting layer (LEL).

In one embodiment, a cyclobutene compound is present in at least one electron-injecting layer or electron-transporting layer that is a non-luminescent layer; that is, it should provide less than 25% of the total device emission. Ideally, it should have substantially no light emission.

The cyclobutene compound contains a cyclobutene nucleus with the numbering system shown below. The cyclobutene nucleus is substituted in the 1-position with a five- or six-membered heteroaromatic ring group containing at least one trivalent nitrogen atom. Desirably the trivalent nitrogen atom is sp² hybridized and has a pair of nonbonding electrons.

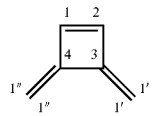

Illustrative examples of suitable heteroaromatic ring groups include a pyridine ring group, a pyrazine ring group, a pyrimidine ring group, a phenanthroline ring group, a triazine ring group, a pyrrole ring group, a carbazole ring group, and a benzothiazole ring group. Illustrative examples are also drawn below.

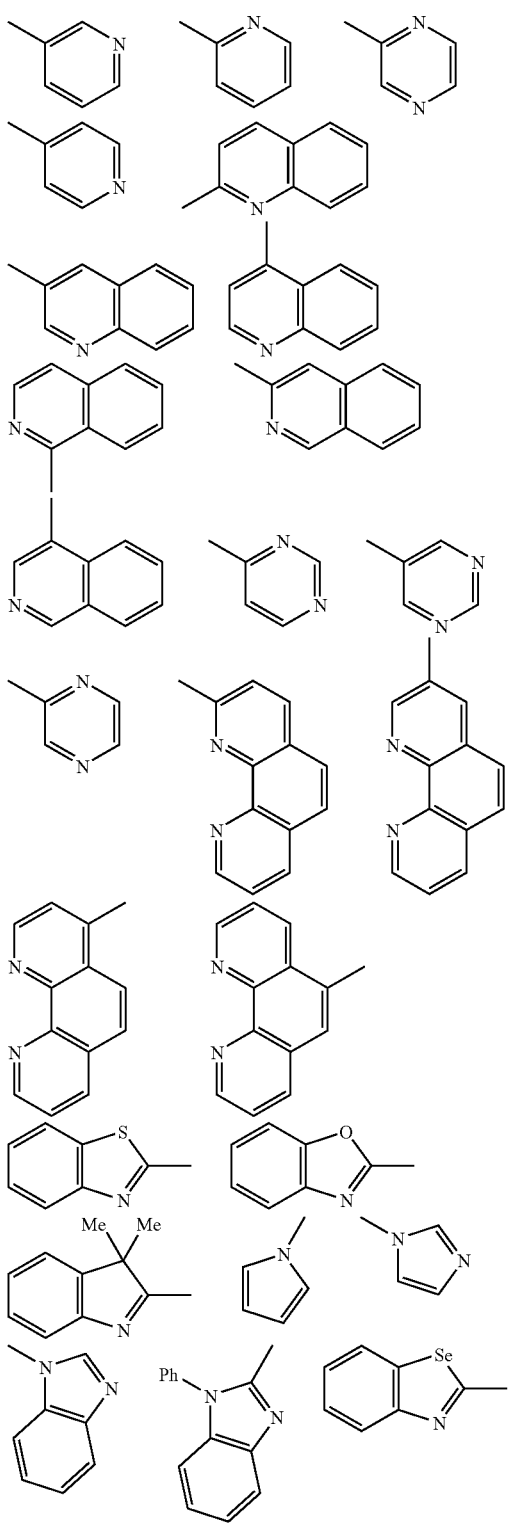

The cyclobutene nucleus is substituted in the 2-position with an aromatic ring group. Suitable aromatic groups include aryl groups having 6-24 carbon atoms, for example, a phenyl group or a naphthyl group. Heteroaryl groups are also suitable, for example, heteroaryl groups wherein the aromatic ring includes N, O, or S atom such as, for example, a pyridine ring group or a thiophene ring group.

In one desirable embodiment, the aromatic ring group in the 2-position is a five- or six-membered heteroaromatic ring group containing at least one trivalent nitrogen atom. Examples of this type of ring group have been described previously. In this case, the substituents in the 1-position and the 2-position can be the same or different. In a further embodiment, they are the same.

In one especially desirable embodiment, the heteroaromatic ring group in the 1-position is an azine group. An azine group is a benzene nucleus in which at least one of the carbon atoms has been replaced with a trivalent nitrogen atom, with the understanding that more than one carbon atom can be replaced with a nitrogen atom. Illustrative examples of azine groups include a pyridine group such as a 2-pyridine group, a 3-pyridine group, a 4-pyridine group, a pyrazine group, a pyrimidine group, a 1,2,3-triazine group, a 1,2,4-triazine group, a 1,3,5-triazine group, and a phenanthroline group. In one embodiment, the azine group is a pyridine group that contains no more than two fused rings, for example, a 3-pyridine or a 2-quinoline. In another suitable embodiment, the cyclobutene compound is substituted in both the 1-position and the 2-position with independently selected azine groups.

In a further desirable embodiment, the heteroaromatic ring group in the 1-position is a five-membered ring group containing a trivalent nitrogen atom such as, for example, a pyrrole group or a carbazole group. In another suitable embodiment, the five-membered ring group also contains at least one additional heteroatom that is divalent or trivalent such as N, O, or S. Illustrative examples include, a benzothiazole ring group, a benzoxazole ring group or a benzimidazole ring group. In a further suitable embodiment, the cyclobutene compound is substituted in both the 1-position and the 2-position with independently selected five-membered ring groups. In a still further embodiment, both the 1-position and the 2-position contain the same five-membered heteroaromatic ring group.

The cyclobutene nucleus is substituted with a first methylene group in the 3-position and a second methylene group in the 4-position, provided the first and second methylene groups are further disubstituted in the 1',1'-positions and the 1'',1''-positions with independently selected aromatic groups. Suitable aromatic groups include aryl groups, for example, a phenyl group or a naphthyl group; and heteroaryl groups such as the five- or six-membered heteroaromatic ring groups including, for example, aromatic rings containing nitrogen, sulfur, or oxygen atoms. In one desirable embodiment, the 1',1'-positions and the 1'',1''-positions are substituted with aryl groups having 6-24 carbon atoms.

Desirably, the cyclobutene compound is not part of a polymer. Suitably, the molecular weight of the cyclobutene compound is less than 1500 daltons, and desirably less than 1000 daltons.

In another embodiment, the cyclobutene compound is represented by Formula (I).

Formula (I)

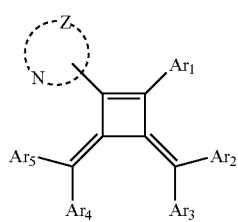

In Formula (I), Z represents the atoms necessary to complete a five- or six-membered aromatic ring containing at least one trivalent nitrogen, examples of suitable rings have been described previously. In one desirable embodiment, Z represents the atoms necessary to complete an azine ring group. Suitable azine groups have also been described previously. In another embodiment, Z represents the atoms necessary to form a pyridine ring group having no more than two fused rings, for example, a 3-pyridine or a 2-quinoline, but not a phenanthroline.

$Ar_1$-$Ar_5$ each represent an independently chosen aryl group having 6-24 carbon atoms, for example, a phenyl group or a naphthyl group; or a heteroaryl group, such as, for example, a pyridyl group or a pyrrolyl group.

In one embodiment, $Ar_1$ represents a five- or six-membered aromatic ring containing at least one trivalent nitrogen, examples of such rings have been described previously. In another embodiment, $Ar_1$ represents the atoms necessary to complete an azine ring group.

In a still further embodiment, $Ar_2$-$Ar_5$ each represents an independently chosen aryl group having 6-24 carbon atoms. $Ar_2$ and $Ar_3$ as well as $Ar_4$ and $Ar_5$ can join together to form an additional ring system such as, for example, a fluorene ring system. In one embodiment, each of $Ar_2$-$Ar_5$ represents the same aryl group.

In a further embodiment, the cyclobutene compound is represented by Formula (IIa).

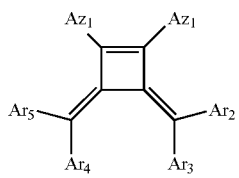

Formula (IIa)

In Formula (IIa), $Az_1$ and $Az_2$ each represent independently selected azine groups. Examples of suitable azine groups have been described previously. $Az_1$ and $Az_2$ can be the same or different, and in one desirable embodiment $Az_1$ and $Az_2$ are the same. Each $Ar_2$-$Ar_5$ represents an independently chosen aryl group having 6-24 carbon atoms such as a naphthyl group or phenyl group. $Ar_2$ and $Ar_3$ as well as $Ar_4$ and $Ar_5$ can join together to form an additional ring system.

In a still further embodiment, the cyclobutene compound is represented by Formula (IIb).

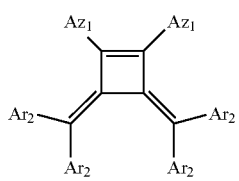

Formula (IIb)

In Formula (IIb), $Az_1$ represents an azine group. In one embodiment, $Az_1$ represents a pyridine group that contains no more than two fused rings, for example, a 2-pyridine or a 1-isoquinoline. In a further embodiment, $Az_1$ represents a pyridine group that contains no fused rings. $Ar_2$ represents an aryl group having 6-24 carbon atoms.

Suitable cyclobutene compounds can be prepared by the general route shown in Schemes A and B. For the structures represented in Schemes A and B, $Ar_1$-$Ar_5$ have been described previously and Het represents a five- or six-membered aromatic ring group containing at least one trivalent nitrogen atom. In Scheme A, a mixture of acetylenes 1 and 2 is treated with triethylamine and methanesulfonyl chloride at low temperatures forming the mesylate derivatives in situ. The reaction mixture is heated in the presence of a base such as potassium carbonate, which affords a mixture of cyclobutenes (3a-3c), as well as additional isomers. The products 3a-3c are separated by column chromatography.

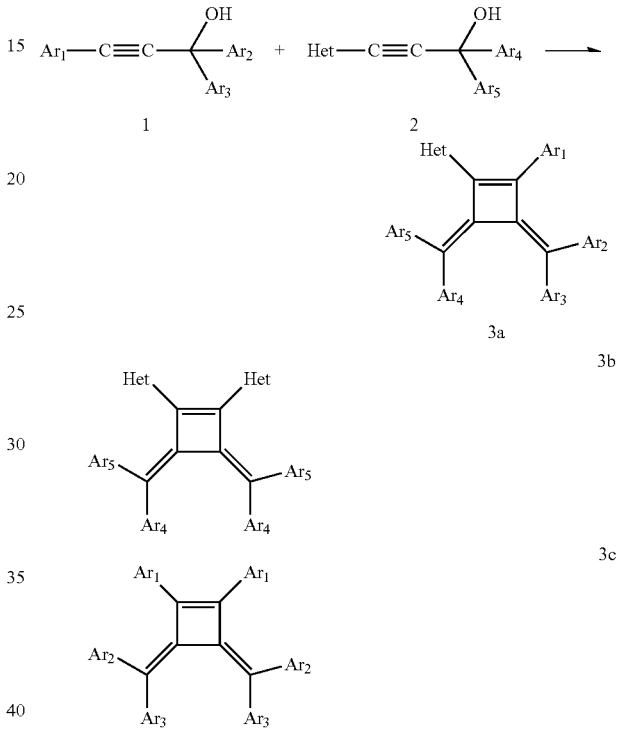

Scheme A

In one embodiment, in order to limit the amount of purification necessary, symmetrical compounds of general formula 5 are preferred and are synthesized according to Scheme B. In Scheme B two equivalents of 4 are combined under conditions described above (Scheme A) to afford compound 5.

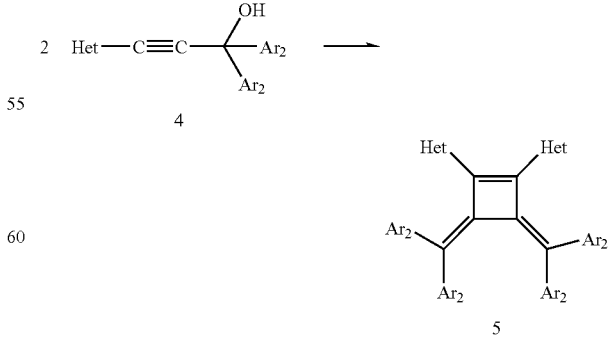

Scheme B

It should be realized that the current invention includes not only examples of molecules represented by generic Formulae I, IIa, and IIb and their specific molecular examples, but also includes all the isomers associated with these structures. In addition, examples of compounds of the invention and their isomers are not limited to those derived from compounds of general structure 1, 2, and 4 but can also include other frameworks and methods of preparation that are useful in producing compounds of Formulae I, IIa, and IIb. In some embodiments, it is desirable to use a cyclobutene compound that consists of a mixture of isomers.

Illustrative, non-limiting, examples of useful cyclobutene compounds are shown below.

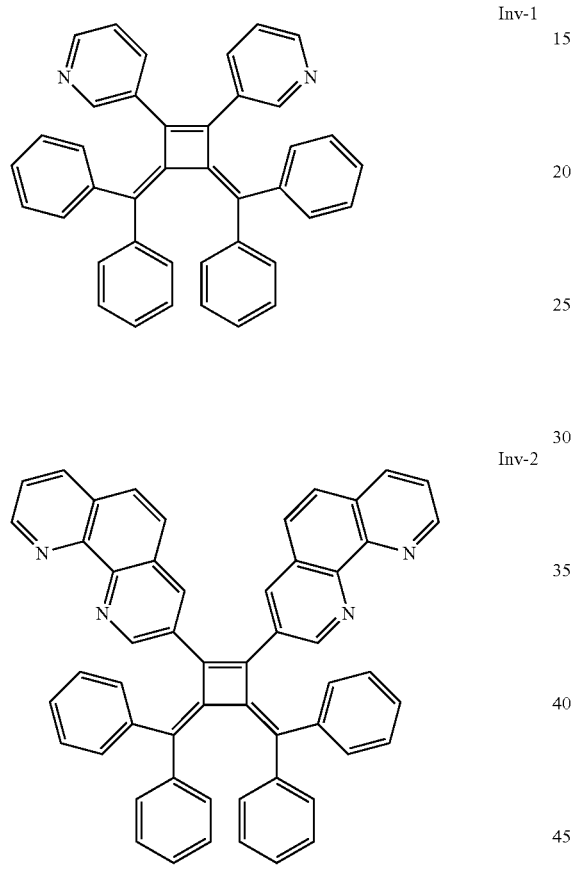

Inv-1

Inv-2

Inv-3

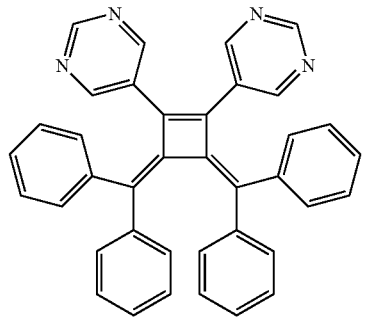

Inv-4

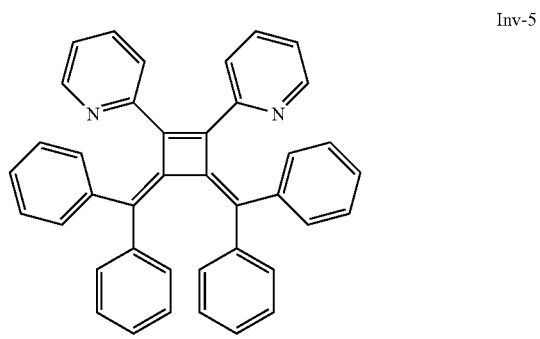

Inv-5

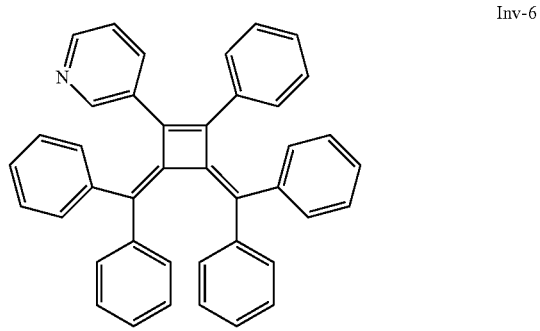

Inv-6

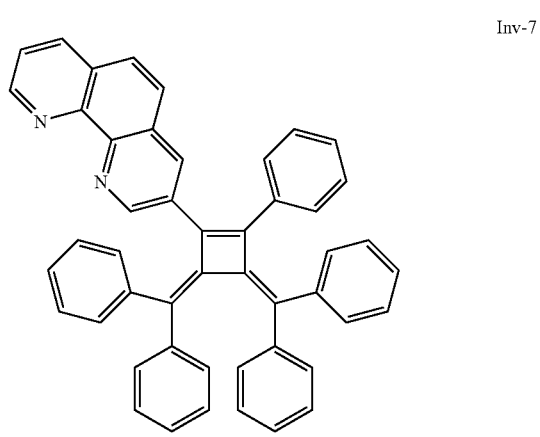

Inv-7

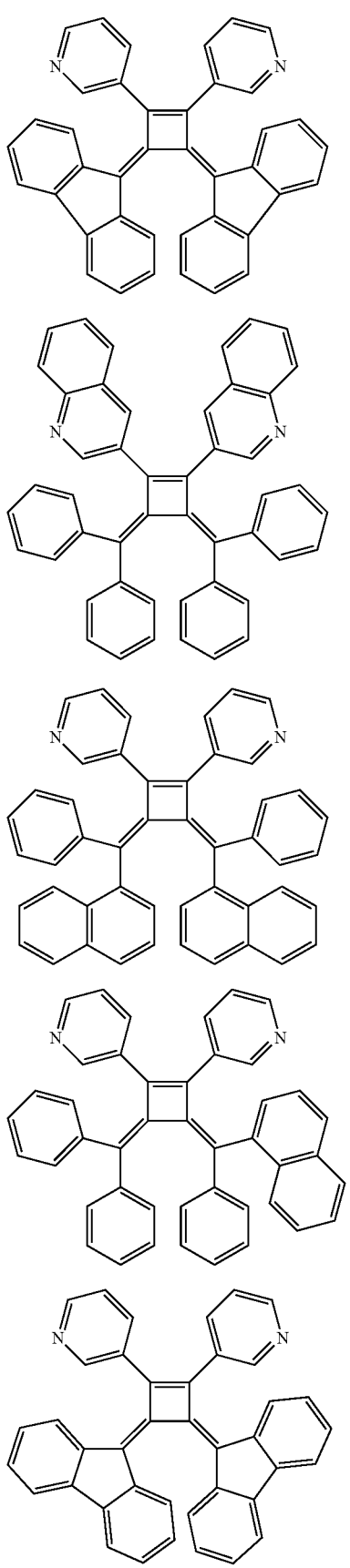
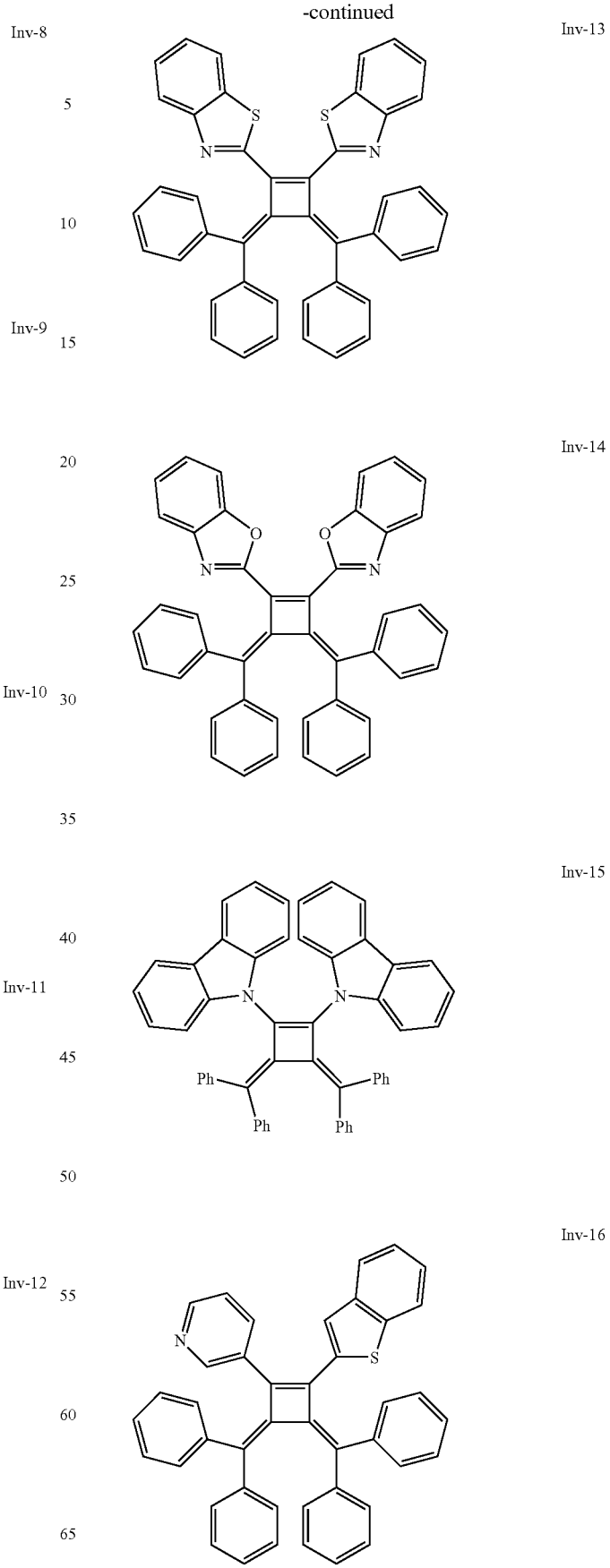

-continued
Inv-17
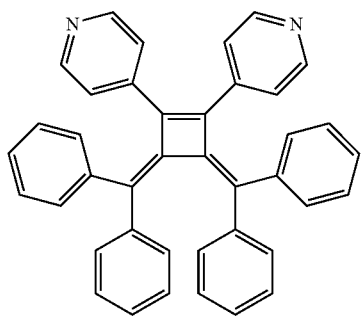
Inv-18
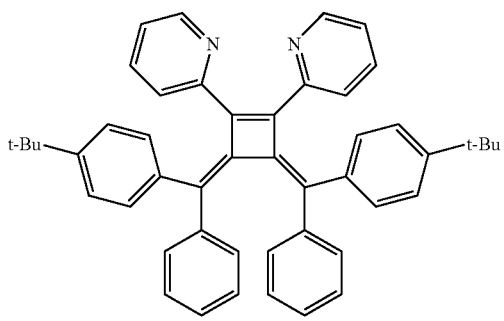
Inv-19
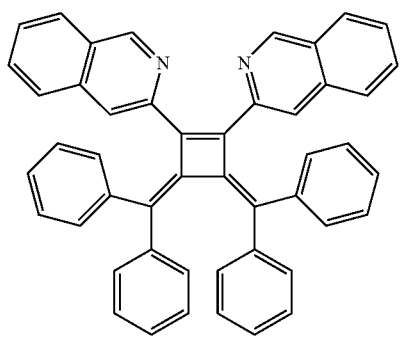
Inv-20
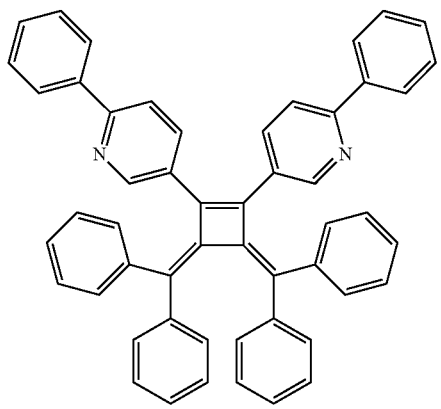
-continued
Inv-21
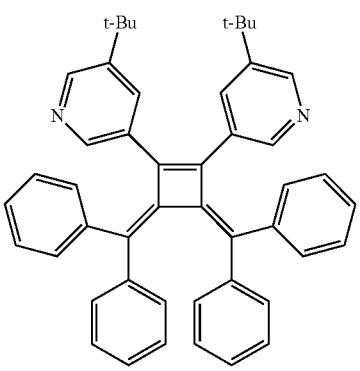
Inv-22
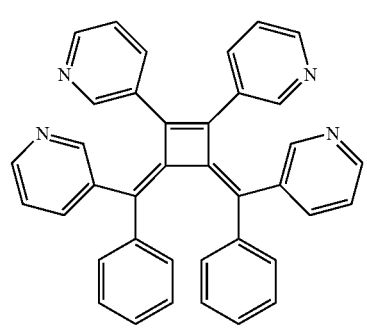
Inv-23
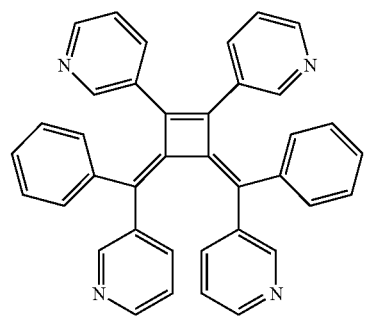
Inv-24
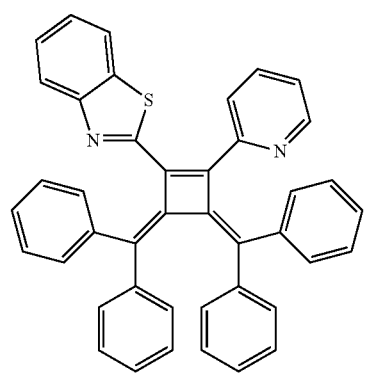

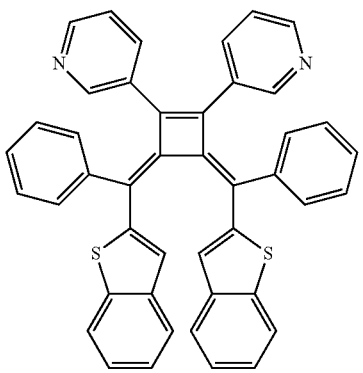

Inv-25

In one highly desirable embodiment of the invention, there is additionally present a second layer, located between the first layer and the cathode. In one embodiment, the second layer is contiguous to the first layer. The second layer contains at least one material chosen from alkali metals, alkali metal compounds, alkaline earth metals, or alkaline earth metal compounds, or combinations thereof. The term "metal compounds" includes organometallic complexes, metal-organic salts, and inorganic salts, oxides and halides. Among the class of metal-containing materials, Li, Na, K, Rb, Cs, Mg, Ca, Sr, Ba, La, Ce, Sm, Eu, Tb, Dy, or Yb, and their compounds, are particularly useful.

Desirably the second layer contains an alkali metal or alkali metal compound. For example, the second layer can be an electron-injecting layer. As an illustrative example, a useful OLED device includes the first layer corresponding to a first electron-injecting layer (EIL1) containing a compound of Formula (I); and the second layer, located between the first layer and the cathode, corresponding to a second electron-injecting layer (EIL2) which contains an alkali metal compound such as LiF. In a further example, the EIL2 is a thin layer of 5 nm or less that contains Li metal.

In one suitable embodiment, the first layer also contains, in addition to the cyclobutene compound, at least one material chosen from alkali metals, alkali metal compounds, alkaline earth metals, or alkaline earth metal compounds, or combinations thereof. In another embodiment, the first layer contains at least one alkali metal or alkali metal compound in addition to the cyclobutene compound. The % volume ratio of alkali metal to cyclobutene compound can be anywhere from 0.1% to 10%, typically 0.5% to 8%, suitably 0.5% to 5%. The % volume ratio of alkali metal compound to cyclobutene compound can be anywhere from 0.1% to 99%, typically 0.5% to 95%, more suitably 10% to 90% and most desirably, 30 to 70%. The first layer can include additional materials.

Alkali metals belong to Group 1 of the periodic table. Of these, lithium is highly preferred. The alkali metal compound can be inorganic or an organometallic compound. For example, inorganic lithium compounds such LiF and Li metal are particularly useful. Useful alkali metal compounds include organic lithium compounds according to Formula (IIIa).

$$(Li^+)_m (Q)_n \quad \text{Formula (IIIa)}$$

In Formula (IIIa), Q is an anionic organic ligand; and m and n are independently selected integers selected to provide a neutral charge on the complex.

The anionic organic ligand Q is most suitably monoanionic and contains at least one ionizable site consisting of oxygen, nitrogen or carbon. In the case of enolates or other tautomeric systems containing oxygen, it will be considered and drawn with the lithium bonded to the oxygen although the lithium can, in fact, be bonded elsewhere to form a chelate. It is also desirable that the ligand contains as at least one nitrogen atom that can form a coordinate or dative bond with the lithium. The integers m and n can be greater than 1 reflecting a known propensity for some organic lithium compounds to form cluster complexes.

Useful alkali metal compounds also include organic lithium compounds represented by Formula (IIIb).

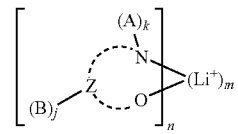

Formula (IIIb)

In Formula (IIIb), Z and the dashed arc represent two to four atoms and the bonds necessary to complete a 5- to 7-membered ring with the lithium cation; each A represents hydrogen or a substituent and each B represents hydrogen or an independently selected substituent on the Z atoms, provided that two or more substituents can combine to form a fused ring or a fused ring system; and j is 0-3 and k is 1 or 2; and m and n are independently selected integers selected to provide a neutral charge on the complex.

Of compounds of Formula (IIIb), it is most desirable that the A and B substituents together form an additional ring system. This additional ring system can further contain additional heteroatoms to form a multidentate ligand with coordinate or dative bonding to the lithium. Desirable heteroatoms are nitrogen or oxygen.

In Formula (IIIb), it is preferred that the oxygen shown is part of a hydroxyl, carboxy or keto group. Examples of suitable nitrogen ligands are 8-hydroxyquinoline, 2-hydroxymethylpyridine, pipecolinic acid or 2-pyridinecarboxylic acid.

Illustrative examples of useful organic alkali metal compounds include the following.

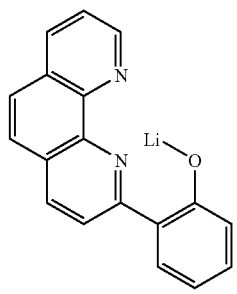

AM-1

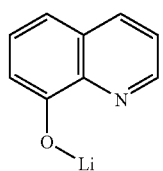

AM-2

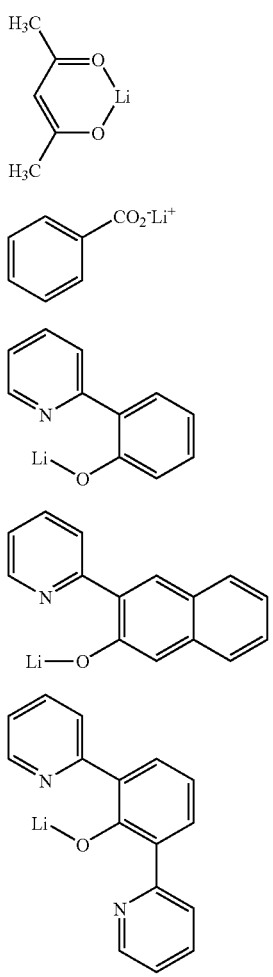

AM-3

AM-4

AM-5

AM-6

AM-7

In a further desirable embodiment, the OLED device includes a third layer located between the first layer and the light-emitting layer, wherein the third layer includes a polycyclic aromatic compound that is capable of transporting electrons. In one embodiment, the third layer is contiguous to the first layer. Both the first and third layers can contain independently selected polycyclic aromatic compounds. The polycyclic aromatic compound can be a hydrocarbon or a heterocycle and includes at least 3 fused rings. Desirably, the polycyclic aromatic compound is a hydrocarbon. In one embodiment, the polycyclic aromatic compound includes a total of at least 6 aromatic rings including at least 3 fused rings. Examples include derivatives of tetracene, pyrene, coronene, chrysene, anthracene, phenanthroline, and bathophenanthroline, diphenylanthracene, fluoranthene, and phenanthrene. Especially useful are polycyclic aromatic hydrocarbons including anthracene derivatives and fluoranthene derivatives. In one embodiment, the third layer also contains at least one material chosen from alkali metals, alkali metal compounds, alkaline earth metals, or alkaline earth metal compounds, or combinations thereof.

As an illustrative example, a useful OLED device includes the first layer, present between the light-emitting layer (LEL) and the cathode, which corresponds to a first electron-injecting layer (EIL1) and contains a cyclobutene compound. The second layer, containing an alkali metal compound and corresponding to a second electron-injecting layer (EIL2), is present between the first layer and the cathode. The third layer corresponding to an electron-transporting layer (ETL) is present between the first layer and the light-emitting layer and includes a polycyclic aromatic hydrocarbon compound. During operation, electrons flow from the cathode to the EIL2 and then are transported into the EIL1 and from there into the ETL and finally to the LEL.

During this process electrons are transferred from the cyclobutene compound of the first layer to the polycyclic aromatic hydrocarbon compound of the third layer. In order to facilitate this transfer, it is desirable to choose the polycyclic aromatic hydrocarbon compound such that its LUMO (Lowest Unoccupied Molecular Orbital) energy level is near the LUMO value of the cyclobutene compound. Desirably, the difference in LUMO energy is an absolute value of 0.3 eV or less, and preferably 0.2 eV or less, and suitably an absolute value of 0.1 eV or less. In a further embodiment, the LUMO energy of the polycyclic aromatic hydrocarbon is the same as or lower than that of the fluoranthene compound, for example, lower (more negative) by 0.05 eV or even 0.1 eV lower or more. LUMO and HOMO energy levels can be determined from redox properties of molecules, which can be measured by well-known literature procedures, such as cyclic voltammetry (CV) and Osteryoung square-wave voltammetry (SWV). For a review of electrochemical measurements, see J. O. Bockris and A. K. N. Reddy, *Modern Electrochemistry*, Plenum Press, New York; and A. J. Bard and L. R. Faulkner, *Electrochemical Methods*, John Wiley & Sons, New York, and references cited therein.

LUMO and HOMO energy levels can also be calculated. Typical calculations are carried out by using the B3LYP method as implemented in the Gaussian 98 (Gaussian, Inc., Pittsburgh, Pa.) computer program. The basis set for use with the B3LYP method is defined as follows: MIDI! for all atoms for which MIDI! is defined, 6-31G* for all atoms defined in 6-31G* but not in MIDI!, and either the LACV3P or the LANL2DZ basis set and pseudopotential for atoms not defined in MIDI! or 6-31G*, with LACV3P being the preferred method. For any remaining atoms, any published basis set and pseudopotential can be used. MIDI!, 6-31 G* and LANL2DZ are used as implemented in the Gaussian98 computer code and LACV3P is used as implemented in the Jaguar 4.1 (Schrodinger, Inc., Portland Oreg.) computer code.

Especially suitable polycyclic aromatic hydrocarbon compounds include anthracene compounds according to Formula (IV).

Formula (IV)

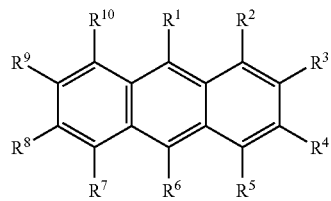

In Formula (IV), $R^1$ and $R^6$ each independently represent an aryl group having 6-24 carbon atoms such as a phenyl group or a naphthyl group. $R^2$-$R^5$ and $R^7$-$R^{10}$ are each independently chosen from hydrogen, alkyl groups from 1-24 carbon atoms or aromatic groups from 6-24 carbon atoms.

In one suitable embodiment $R^1$ and $R^6$ each represent an independently selected phenyl group, biphenyl group, or napthyl group. $R^3$ represents hydrogen or a phenyl or napthyl group. $R^2$, $R^4$, $R^5$, $R^7$-$R^{10}$ represent hydrogen.

Illustrative examples of useful anthracenes are listed below.

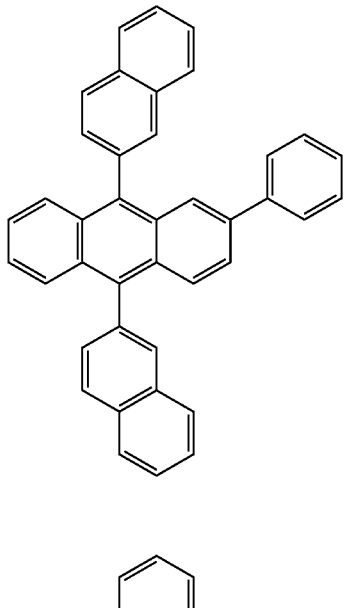
P-1

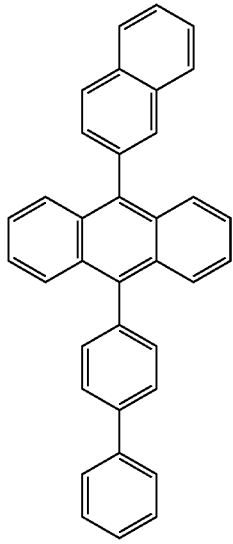
P-2

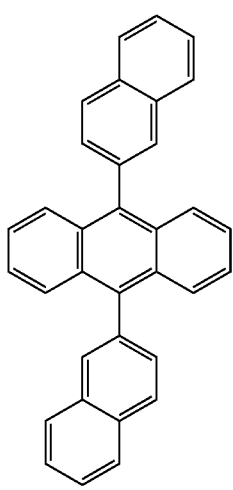
P-3

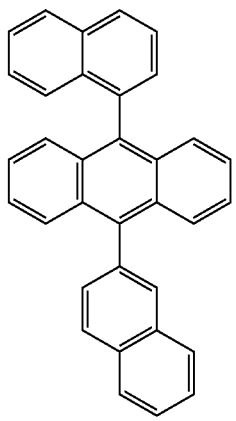
P-4

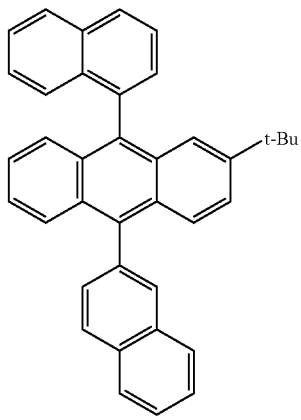
P-5

Fluoranthenes according to Formula (V) are also suitable polycyclic aromatic hydrocarbon compounds.

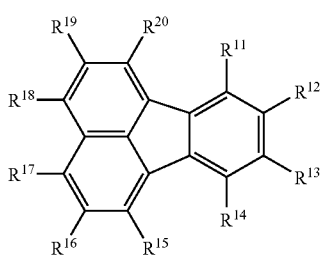
Formula (V)

In Formula (V), $R^{11}$-$R^{20}$ are independently chosen from hydrogen, alkyl groups from 1-24 carbon atoms or aromatic groups from 6-24 carbon atoms provided adjacent groups can combine to form fused aromatic rings.

Especially suitable fluoranthene derivatives are those described in above cited, commonly assigned U.S. patent application Ser. No. 11/924,631, the disclosure of which is incorporated herein by reference. For example, 7,10-diaryl-fluoranthene derivatives represented according to Formulae (VI) and (VII) are useful.

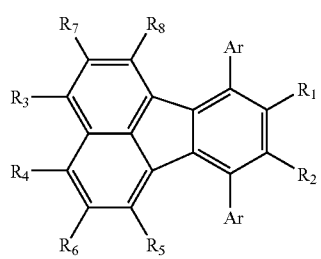

Formula (VI)

In Formula (VI) Ar represents the aromatic rings containing 6 to 24 carbon atoms substituted on the fluoranthene nucleus and can be the same or different; and $R_1$-$R_8$ are individually selected from hydrogen and aromatic rings containing 6 to 24 carbon atoms with the provision that no two adjacent $R_1$-$R_8$ substituents can join to form a ring annulated to the fluoranthene nucleus.

In Formula (VI), the Ar group(s) are carbocyclic groups. The Ar group(s) cannot be fused with the floranthene nucleus and are connected only by one single bond. Preferred Ar groups are phenyl or napthyl with phenyl being particularly preferred. Derivatives where the Ar groups are the same are also desirable.

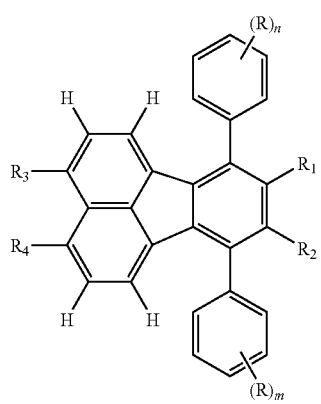

Formula (VII)

In Formula (VII), $R_1$, $R_2$, $R_3$ and $R_4$ are independently hydrogen or an aromatic group containing 6 to 24 carbon atoms with the provision that any adjacent $R_1$-$R_4$ is not part of an annulated aromatic ring system; R is hydrogen or an optional substituent; and n and m are independently 1-5.

Illustrative examples of useful electron-transporting fluoranthene derivatives are shown below.

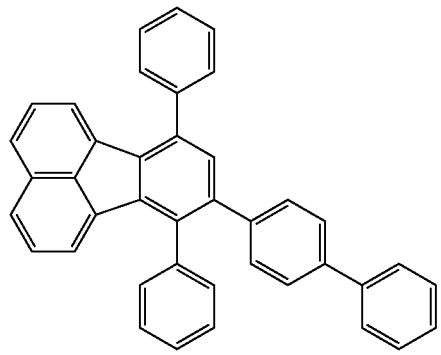

FA-1

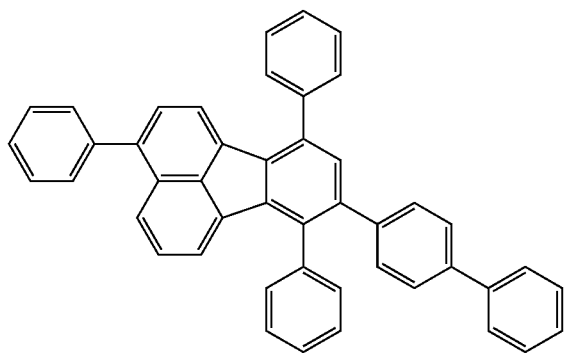

FA-2

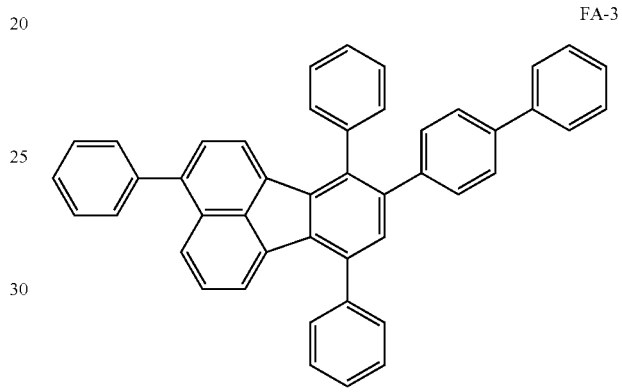

FA-3

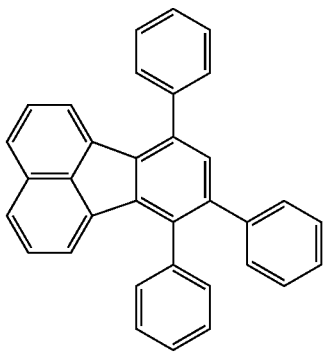

FA-4

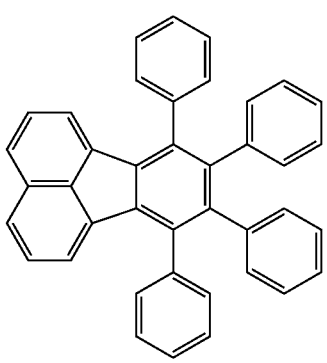

FA-5

-continued

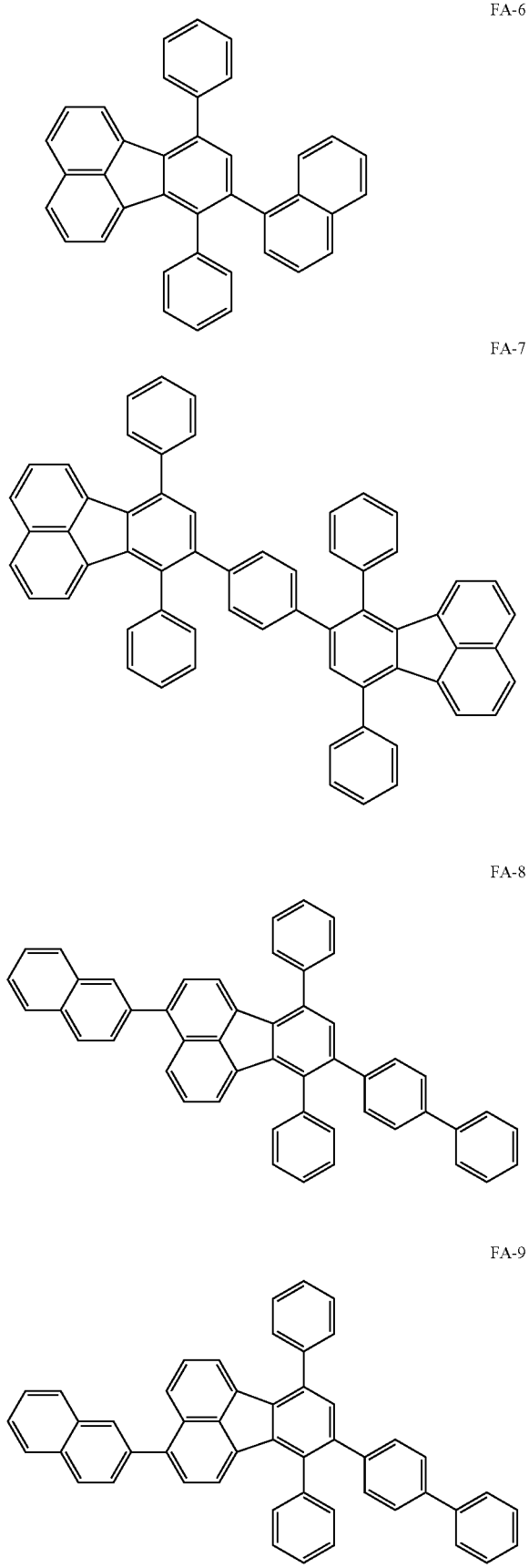

FA-6
FA-7
FA-8
FA-9

-continued

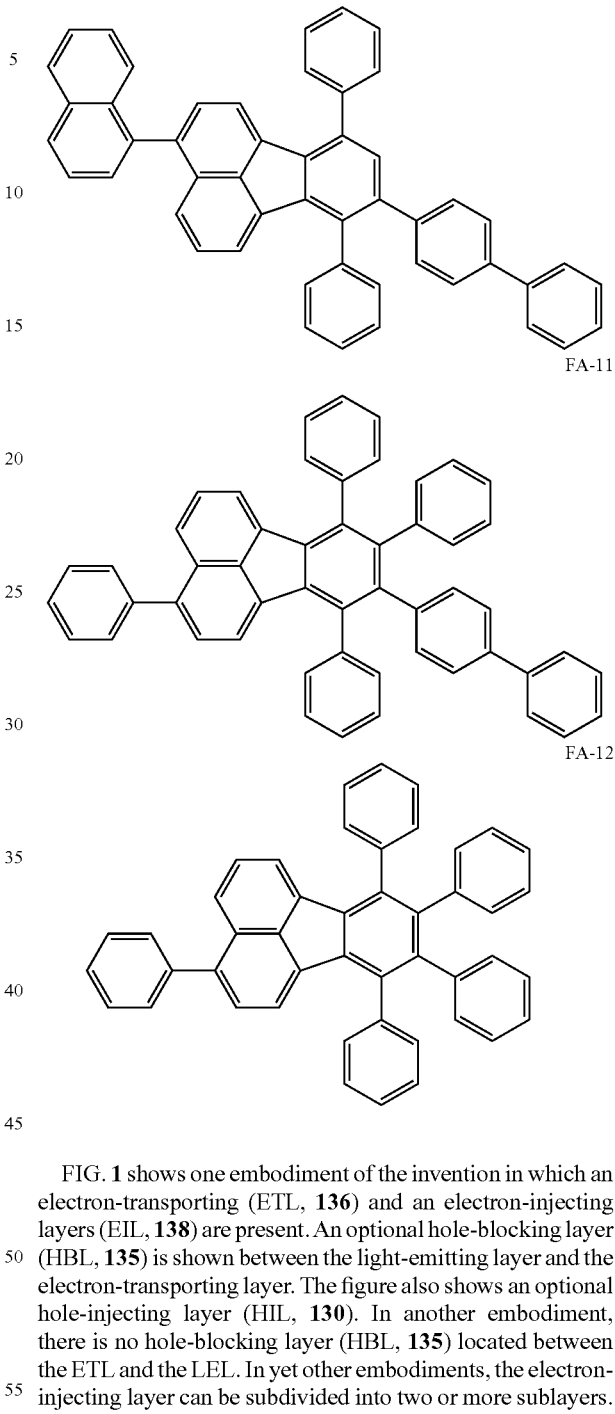

FA-10
FA-11
FA-12

FIG. 1 shows one embodiment of the invention in which an electron-transporting (ETL, 136) and an electron-injecting layers (EIL, 138) are present. An optional hole-blocking layer (HBL, 135) is shown between the light-emitting layer and the electron-transporting layer. The figure also shows an optional hole-injecting layer (HIL, 130). In another embodiment, there is no hole-blocking layer (HBL, 135) located between the ETL and the LEL. In yet other embodiments, the electron-injecting layer can be subdivided into two or more sublayers.

In one illustrative example, the OLED device has no hole-blocking layer and only one hole-injecting, electron-injecting and electron-transporting layer. The cyclobutene compound is present in the EIL (138) and an organic lithium compound is also present in the EIL and a polycyclic aromatic hydrocarbon compound is present in the ETL (136).

In another illustrative example, the EIL (138) is further divided into two sublayers (not shown), a first electron-injecting layer (EIL1) adjacent to the ETL (136) and a second electron-injecting layer (EIL2) located between the EIL1 and the cathode. The cyclobutene compound is present in the EIL1 and a lithium metal compound is present in the EIL2 and a polycyclic aromatic hydrocarbon compound is present in the ETL (136).

Examples of preferred combinations of the invention are those wherein the cyclobutene compound is selected from Inv-1, Inv-2, Inv-3, Inv-4, and Inv-5 or mixtures thereof, the alkali metal is Li metal or the alkali metal compound is selected from LiF, AM-1, AM-2 and AM-3 or mixtures thereof, and the polycyclic aromatic hydrocarbon compound (when present) is selected from FA-1, FA-2, FA-3, FA-4, P-2, and P-4 or mixtures thereof.

In one suitable embodiment the EL device includes a way of emitting white light, which can include complementary emitters, a white emitter, or a filtering structure. This invention can be used in so-called stacked device architecture, for example, as taught in U.S. Pat. Nos. 5,703,436 and 6,337,492. Embodiments of the current invention can be used in stacked devices that include solely fluorescent elements to produce white light. The device can also include combinations of fluorescent emitting materials and phosphorescent emitting materials (sometimes referred to as hybrid OLED devices). To produce a white emitting device, ideally the hybrid fluorescent/phosphorescent device would include a blue fluorescent emitter and proper proportions of a green and red phosphorescent emitter, or other color combinations suitable to make white emission. However, hybrid devices having non-white emission can also be useful by themselves. Hybrid fluorescent/phosphorescent elements having non-white emission can also be combined with additional phosphorescent elements in series in a stacked OLED. For example, white emission can be produced by one or more hybrid blue fluorescent/red phosphorescent elements stacked in series with a green phosphorescent element using p/n junction connectors as disclosed in Tang et al. U.S. Pat. No. 6,936,961B2.

In one desirable embodiment the EL device is part of a display device. In another suitable embodiment the EL device is part of an area lighting device.

The EL device of the invention is useful in any device where stable light emission is desired such as a lamp or a component in a static or motion imaging device, such as a television, cell phone, DVD player, or computer monitor.

As used herein and throughout this application, the term carbocyclic and heterocyclic rings or groups are generally as defined by the *Grant & Hackh's Chemical Dictionary*, Fifth Edition, McGraw-Hill Book Company. A carbocyclic ring is any aromatic or non-aromatic ring system containing only carbon atoms and a heterocyclic ring is any aromatic or non-aromatic ring system containing both carbon and non-carbon atoms such as nitrogen (N), oxygen (O), sulfur (S), phosphorous (P), silicon (Si), gallium (Ga), boron (B), beryllium (Be), indium (In), aluminum (Al), and other elements found in the periodic table useful in forming ring systems. For the purpose of this invention, also included in the definition of a heterocyclic ring are those rings that include coordinate bonds. The definition of a coordinate or dative bond can be found in *Grant & Hackh's Chemical Dictionary*, pages 91 and 153. In essence, a coordinate bond is formed when electron rich atoms such as O or N, donate a pair of electrons to electron deficient atoms or ions such as aluminum, boron or alkali metal ions such $Li^+$, $Na^+$, $K^+$ and $Cs^+$. One such example is found in tris(8-quinolinolato)aluminum(III), also referred to as Alq, wherein the nitrogen on the quinoline moiety donates its lone pair of electrons to the aluminum atom thus forming the heterocycle and hence providing Alq with a total of 3 fused rings. The definition of a ligand, including a multidentate ligand, can be found in *Grant & Hackh's Chemical Dictionary*, pages 337 and 176, respectively.

Unless otherwise specifically stated, use of the term "substituted" or "substituent" means any group or atom other than hydrogen. Additionally, when the term "group" is used, it means that when a substituent group contains a substitutable hydrogen, it is also intended to encompass not only the substituent's unsubstituted form, but also its form further substituted with any substituent group or groups as herein mentioned, so long as the substituent does not destroy properties necessary for device utility. Suitably, a substituent group can be halogen or can be bonded to the remainder of the molecule by an atom of carbon, silicon, oxygen, nitrogen, phosphorous, sulfur, selenium, or boron. The substituent can be, for example, halogen, such as chloro, bromo or fluoro; nitro; hydroxyl; cyano; carboxyl; or groups which can be further substituted, such as alkyl, including straight or branched chain or cyclic alkyl, such as methyl, trifluoromethyl, ethyl, t-butyl, 3-(2,4-di-t-pentylphenoxy)propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecyl-benzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl, N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1(N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which can be substituted and which contain a 3 to 7 membered heterocyclic ring composed of carbon atoms and at least one hetero atom selected from the group consisting of oxygen, nitrogen, sulfur, phosphorous, or boron, such as 2-furyl, 2-thienyl, 2-benzimidazolyloxy or 2-benzothiazolyl; quaternary ammonium, such as triethylammonium; quaternary phosphonium, such as triphenylphosphonium; and silyloxy, such as trimethylsilyloxy.

If desired, the substituents can themselves be further substituted one or more times with the described substituent groups. The particular substituents used can be selected by those skilled in the art to attain desirable properties for a specific application and can include, for example, electron-withdrawing groups, electron-donating groups, and steric groups. When a molecule can have two or more substituents, the substituents can be joined together to form a ring such as a fused ring unless otherwise provided. Generally, the above groups and substituents thereof can include those having up to 48 carbon atoms, typically 1 to 36 carbon atoms and usually less than 24 carbon atoms, but greater numbers are possible depending on the particular substituents selected.

The following is the description of the layer structure, material selection, and fabrication process for OLED devices.

General OLED Device Architecture

The present invention can be employed in many OLED configurations using small molecule materials, oligomeric materials, polymeric materials, or combinations thereof. These include from very simple structures having a single anode and cathode to more complex devices, such as passive matrix displays having orthogonal arrays of anodes and cathodes to form pixels, and active-matrix displays where each pixel is controlled independently, for example, with thin film transistors (TFTs). There are numerous configurations of the organic layers wherein the present invention is successfully practiced. For this invention, essential requirements are a cathode, an anode, a LEL, an ETL and a HIL.

As previously discussed, one embodiment according to the present invention and especially useful for a small molecule device is shown in FIG. 1. an OLED 100 contains a substrate 110, an anode 120, a hole-injecting layer 130, a hole-transporting layer 132, a light-emitting layer 134, a hole-blocking layer 135, an electron-transporting layer 136, an electron-injecting layer 138 and a cathode 140. In some other embodiments, there are optional spacer layers on either side of the LEL. These spacer layers do not typically contain light emissive materials. All of these layer types will be described in detail below. Note that the substrate can alternatively be located adjacent to the cathode, or the substrate can actually constitute the anode or cathode. Also, the total combined thickness of the organic layers is preferably less than 500 nm.

The anode and cathode of the OLED are connected to a voltage/current source 150, through electrical conductors 160. Applying a potential between the anode and cathode such that the anode is at a more positive potential than the cathode operates the OLED. Holes are injected into the organic EL element from the anode. Enhanced device stability can sometimes be achieved when the OLED is operated in an AC mode where, for some time period in cycle, the potential bias is reversed and no current flows. An example of an AC driven OLED is described in U.S. Pat. No. 5,552,678.

Anode

When the desired EL emission is viewed through the anode, anode 120 should be transparent or substantially transparent to the emission of interest. Common transparent anode materials used in this invention are indium-tin oxide (ITO), indium-zinc oxide (IZO) and tin oxide, but other metal oxides can work including, but not limited to, aluminum- or indium-doped zinc oxide, magnesium-indium oxide, and nickel-tungsten oxide. In addition to these oxides, metal nitrides, such as gallium nitride, and metal selenides, such as zinc selenide, and metal sulfides, such as zinc sulfide, can be used as the anode 120. For applications where EL emission is viewed only through the cathode 140, the transmissive characteristics of the anode 120 are immaterial and any conductive material can be used, transparent, opaque or reflective. Example conductors for this application include, but are not limited to, gold, iridium, molybdenum, palladium, and platinum. Typical anode materials, transmissive or otherwise, have a work function of 4.1 eV or greater. Desired anode materials are commonly deposited by any suitable means such as evaporation, sputtering, chemical vapor deposition, or electrochemical means. Anodes can be patterned using well-known photolithographic processes. Optionally, anodes can be polished prior to application of other layers to reduce surface roughness so as to minimize short circuits or enhance reflectivity.

Hole Injection Layer

Although it is not always necessary, it is often useful to provide an HIL in the OLEDs. HIL 130 in the OLEDs can serve to facilitate hole injection from the anode into the HTL, thereby reducing the drive voltage of the OLEDs. Suitable materials for use in HIL 130 include, but are not limited to, porphyrinic compounds as described in U.S. Pat. No. 4,720,432 and some aromatic amines, for example, 4,4',4''-tris[(3-ethylphenyl)phenylamino]triphenylamine (m-TDATA). Alternative hole-injecting materials reportedly useful in OLEDs are described in EP 0 891 121 A1 and EP 1 029 909 A1. Aromatic tertiary amines discussed below can also be useful as hole-injecting materials. Other useful hole-injecting materials such as dipyrazino[2,3-f:2',3'-h]quinoxalinehexacarbonitrile are described in U.S. Patent Application Publication 2004/0113547 A1 and U.S. Pat. No. 6,720,573. In addition, a p-type doped organic layer is also useful for the HIL as described in U.S. Pat. No. 6,423,429. The term "p-type doped organic layer" means that this layer has semiconducting properties after doping, and the electrical current through this layer is substantially carried by the holes. The conductivity is provided by the formation of a charge-transfer complex as a result of hole transfer from the dopant to the host material.

The thickness of the HIL 130 is in the range of from 0.1 nm to 200 nm, preferably, in the range of from 0.5 nm to 150 nm.

Hole Transport Layer

The HTL 132 contains at least one hole-transporting material such as an aromatic tertiary amine, where the latter is understood to be a compound containing at least one trivalent nitrogen atom that is bonded only to carbon atoms, at least one of which is a member of an aromatic ring. In one form the aromatic tertiary amine is an arylamine, such as a monoarylamine, diarylamine, triarylamine, or a polymeric arylamine. Exemplary monomeric triarylamines are illustrated by Klupfel et al. U.S. Pat. No. 3,180,730. Other suitable triarylamines substituted with one or more vinyl radicals or at least one active hydrogen-containing group are disclosed by Brantley, et al. in U.S. Pat. Nos. 3,567,450 and 3,658,520.

A more preferred class of aromatic tertiary amines are those which include at least two aromatic tertiary amine moieties as described in U.S. Pat. Nos. 4,720,432 and 5,061,569. Such compounds include those represented by structural Formula (A)

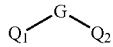
(A)

wherein:

$Q_1$ and $Q_2$ are independently selected aromatic tertiary amine moieties; and G is a linking group such as an arylene, cycloalkylene, or alkylene group of a carbon to carbon bond.

In one embodiment, at least one of $Q_1$ or $Q_2$ contains a polycyclic fused ring structure, e.g., a naphthalene. When G is an aryl group, it is conveniently a phenylene, biphenylene, or naphthalene moiety.

A useful class of triarylamines satisfying structural Formula A and containing two triarylamine moieties is represented by structural Formula (B)

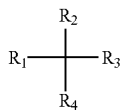
(B)

wherein:

$R_1$ and $R_2$ each independently represents a hydrogen atom, an aryl group, or an alkyl group or $R_1$ and $R_2$ together represent the atoms completing a cycloalkyl group; and $R_3$ and $R_4$ each independently represents an aryl group, which is in turn substituted with a diaryl substituted amino group, as indicated by structural Formula (C)

(C)

wherein:

$R_5$ and $R_6$ are independently selected aryl groups. In one embodiment, at least one of $R_5$ or $R_6$ contains a polycyclic fused ring structure, e.g., a naphthalene.

Another class of aromatic tertiary amines are the tetraaryldiamines. Desirable tetraaryldiamines include two diarylamino groups, such as indicated by Formula (C), linked through an arylene group. Useful tetraaryldiamines include those represented by Formula (D)

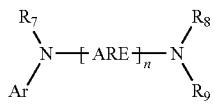
(D)

wherein:

each ARE is an independently selected arylene group, such as a phenylene or anthracene moiety;

n is an integer of from 1 to 4; and

Ar, $R_7$, $R_8$, and $R_9$ are independently selected aryl groups. In a typical embodiment, at least one of Ar, $R_7$, $R_8$, and $R_9$ is a polycyclic fused ring structure, e.g., a naphthalene.

Another class of the hole-transporting material comprises a material of formula (E):

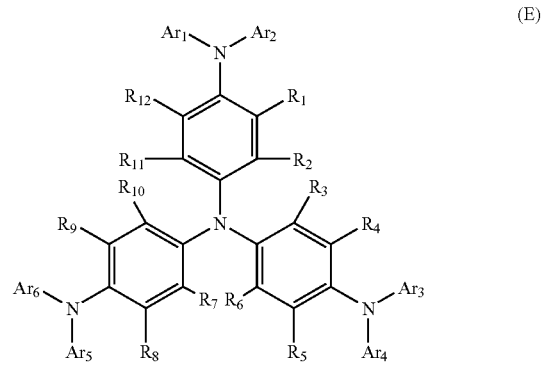
(E)

In formula (E), $Ar_1$-$Ar_6$ independently represent aromatic groups, for example, phenyl groups or tolyl groups;

$R_1$-$R_{12}$ independently represent hydrogen or independently selected substituent, for example an alkyl group containing from 1 to 4 carbon atoms, an aryl group, a substituted aryl group.

The various alkyl, alkylene, aryl, and arylene moieties of the foregoing structural Formulae (A), (B), (C), (D), and (E) can each in turn be substituted. Typical substituents include alkyl groups, alkoxy groups, aryl groups, aryloxy groups, and halogen such as fluoride, chloride, and bromide. The various alkyl and alkylene moieties typically contain from about 1 to 6 carbon atoms. The cycloalkyl moieties can contain from 3 to about 10 carbon atoms, but typically contain five, six, or seven ring carbon atoms, e.g. cyclopentyl, cyclohexyl, and cycloheptyl ring structures. The aryl and arylene moieties are typically phenyl and phenylene moieties.

The HTL is formed of a single or a mixture of aromatic tertiary amine compounds. Specifically, one can employ a triarylamine, such as a triarylamine satisfying the Formula (B), in combination with a tetraaryldiamine, such as indicated by Formula (D). When a triarylamine is employed in combination with a tetraaryldiamine, the latter is positioned as a layer interposed between the triarylamine and the electron injecting and transporting layer. Aromatic tertiary amines are useful as hole-injecting materials also. Illustrative of useful aromatic tertiary amines are the following:

1,1-bis(4-di-p-tolylaminophenyl)cyclohexane;
1,1-bis(4-di-p-tolylaminophenyl)-4-phenylcyclohexane;
1,5-bis[N-(1-naphthyl)-N-phenylamino]naphthalene;
2,6-bis(di-p-tolylamino)naphthalene;
2,6-bis[di-(1-naphthyl)amino]naphthalene;
2,6-bis[N-(1-naphthyl)-N-(2-naphthyl)amino]naphthalene;
2,6-bis[N,N-di(2-naphthyl)amine]fluorene;
4-(di-p-tolylamino)-4'-[4(di-p-tolylamino)-styryl]stilbene;
4,4'-bis(diphenylamino)quadriphenyl;
4,4"-bis[N-(1-anthryl)-N-phenylamino]-p-terphenyl;
4,4'-bis[N-(1-coronenyl)-N-phenylamino]biphenyl;
4,4'-bis[N-(1-naphthyl)-N-phenylamino]biphenyl (NPB);
4,4'-bis[N-(1-naphthyl)-N-(2-naphthyl)amino]biphenyl (TNB);

4,4"-bis[N-(1-naphthyl)-N-phenylamino]p-terphenyl;
4,4'-bis[N-(2-naphthacenyl)-N-phenylamino]biphenyl;
4,4'-bis[N-(2-naphthyl)-N-phenylamino]biphenyl;
4,4'-bis[N-(2-perylenyl)-N-phenylamino]biphenyl;
4,4'-bis[N-(2-phenanthryl)-N-phenylamino]biphenyl;
4,4'-bis[N-(2-pyrenyl)-N-phenylamino]biphenyl;
4,4'-bis[N-(3-acenaphthenyl)-N-phenylamino]biphenyl;
4,4'-bis[N-(3-methylphenyl)-N-phenylamino]biphenyl (TPD);
4,4'-bis[N-(8-fluoranthenyl)-N-phenylamino]biphenyl;
4,4'-bis[N-(9-anthryl)-N-phenylamino]biphenyl;
4,4'-bis{N-phenyl-N-[4-(1-naphthyl)-phenyl]amino}biphenyl;
4,4'-bis[N-phenyl-N-(2-pyrenyl)amino]biphenyl;
4,4',4"-tris[(3-methylphenyl)phenylamino]triphenylamine (m-TDATA);
Bis(4-dimethylamino-2-methylphenyl)-phenylmethane;
N-phenylcarbazole;
N,N'-bis[4-([1,1'-biphenyl]-4-ylphenylamino)phenyl]-N,N'-di-1-naphthalenyl-[1,1'-biphenyl]-4,4'-diamine;
N,N'-bis[4-(di-1-naphthalenylamino)phenyl]-N,N'-di-1-naphthalenyl-[1,1'-biphenyl]-4,4'-diamine;
N,N'-bis[4-[(3-methylphenyl)phenylamino]phenyl]-N,N'-diphenyl-[1,1'-biphenyl]-4,4'-diamine;
N,N-bis[4-(diphenylamino)phenyl]-N',N'-diphenyl-[1,1'-biphenyl]-4,4'-diamine;
N,N'-di-1-naphthalenyl-N,N'-bis[4-(1-naphthalenylphenylamino)phenyl]-[1,1'-biphenyl]-4,4'-diamine;
N,N'-di-1-naphthalenyl-N,N'-bis[4-(2-naphthalenylphenylamino)phenyl]-[1,1'-biphenyl]-4,4'-diamine;
N,N,N-tri(p-tolyl)amine;
N,N,N',N'-tetra-p-tolyl-4-4'-diaminobiphenyl;
N,N,N',N'-tetraphenyl-4,4'-diaminobiphenyl;
N,N,N',N'-tetra-1-naphthyl-4,4'-diaminobiphenyl;
N,N,N',N'-tetra-2-naphthyl-4,4'-diaminobiphenyl; and
N,N,N',N'-tetra(2-naphthyl)-4,4"-diamino-p-terphenyl.

Another class of useful hole-transporting materials includes polycyclic aromatic compounds as described in EP 1 009 041. Tertiary aromatic amines with more than two amine groups can be used including oligomeric materials. In addition, polymeric hole-transporting materials are used such as poly(N-vinylcarbazole) (PVK), polythiophenes, polypyrrole, polyaniline, and copolymers such as poly(3,4-ethylenedioxythiophene)/poly(4-styrenesulfonate) also called PEDOT/PSS.

The thickness of the HTL 132 is in the range of from 5 nm to 200 nm, preferably, in the range of from 10 nm to 150 nm.
Exciton Blocking Layer (EBL)

An optional exciton- or electron-blocking layer can be present between the HTL and the LEL (not shown in FIG. 1). Some suitable examples of such blocking layers are described in U.S. Patent Application Publication No. 2006/0134460A1.
Light Emitting Layer As more fully described in U.S. Pat. Nos. 4,769,292 and 5,935,721, the light-emitting layer(s) (LEL) 134 of the organic EL element shown in FIG. 1 includes a luminescent, fluorescent or phosphorescent material where electroluminescence is produced as a result of electron-hole pair recombination in this region. The light-emitting layer can include a single material, but more commonly consists of non-electroluminescent compounds (generally referred to as the host) doped with an electroluminescent guest compound (generally referred to as the dopant) or compounds where light emission comes primarily from the electroluminescent compound and can be of any color. Electroluminescent compounds can be coated as 0.01 to 50% into the non-electroluminescent component material, but typically coated as 0.01 to 30% and more typically coated as 0.01 to 15% into the non-electroluminescent component. The thickness of the LEL can be any suitable thickness. It can be in the range of from 0.1 mm to 100 mm.

An important relationship for choosing a dye as a electroluminescent component is a comparison of the bandgap potential which is defined as the energy difference between the highest occupied molecular orbital and the lowest unoccupied molecular orbital of the molecule. For efficient energy transfer from the non-electroluminescent compound to the electroluminescent compound molecule, a necessary condition is that the band gap of the electroluminescent compound is smaller than that of the non-electroluminescent compound or compounds. Thus, the selection of an appropriate host material is based on its electronic characteristics relative to the electronic characteristics of the electroluminescent compound, which itself is chosen for the nature and efficiency of the light emitted. As described below, fluorescent and phosphorescent dopants typically have different electronic characteristics so that the most appropriate hosts for each can be different. However in some cases, the same host material can be useful for either type of dopant.

Non-electroluminescent compounds and emitting molecules known to be of use include, but are not limited to, those disclosed in U.S. Pat. Nos. 5,141,671; 5,150,006; 5,151,629; 5,405,709; 5,484,922; 5,593,788; 5,645,948; 5,683,823; 5,755,999; 5,928,802; 5,935,720; 5,935,721, and 6,020,078.
a) Phosphorescent Light Emitting Layers Suitable hosts for phosphorescent LELs should be selected so that transfer of a triplet exciton can occur efficiently from the host to the phosphorescent dopant(s) but cannot occur efficiently from the phosphorescent dopant(s) to the host. Therefore, it is highly desirable that the triplet energy of the host be higher than the triplet energies of phosphorescent dopant. Generally speaking, a large triplet energy implies a large optical band gap. However, the band gap of the host should not be chosen so large as to cause an unacceptable barrier to injection of holes into the fluorescent blue LEL and an unacceptable increase in the drive voltage of the OLED. The host in a phosphorescent LEL can include any of the aforementioned hole-transporting material used for the HTL 132, as long as it has a triplet energy higher than that of the phosphorescent dopant in the layer. The host used in a phosphorescent LEL can be the same as or different from the hole-transporting material used in the HTL 132. In some cases, the host in the phosphorescent LEL can also suitably include an electron-transporting material (it will be discussed thereafter), as long as it has a triplet energy higher than that of the phosphorescent dopant.

In addition to the aforementioned hole-transporting materials in the HTL 132, there are several other classes of hole-transporting materials suitable for use as the host in a phosphorescent LEL.

One desirable host includes a hole-transporting material of formula (F):

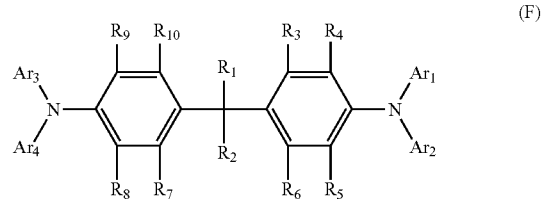

(F)

In formula (F), $R_1$ and $R_2$ represent substituents, provided that $R_1$ and $R_2$ can join to form a ring. For example, $R_1$ and $R_2$ can be methyl groups or join to form a cyclohexyl ring;

$Ar_1$-$Ar_4$ represent independently selected aromatic groups, for example phenyl groups or tolyl groups;

$R_3$-$R_{10}$ independently represent hydrogen, alkyl, substituted alkyl, aryl, substituted aryl group.

Examples of suitable materials include, but are not limited to:

1,1-Bis(4-(N,N-di-p-tolylamino)phenyl)cyclohexane (TAPC);
1,1-Bis(4-(N,N-di-p-tolylamino)phenyl)cyclopentane;
4,4'-(9H-fluoren-9-ylidene)bis[N,N-bis(4-methylphenyl)-benzenamine;
1,1-Bis(4-(N,N-di-p-tolylamino)phenyl)-4-phenylcyclohexane;
1,1-Bis(4-(N,N-di-p-tolylamino)phenyl)-4-methylcyclohexane;
1,1-Bis(4-(N,N-di-p-tolylamino)phenyl)-3-phenylpropane;
Bis[4-(N,N-diethylamino)-2-methylphenyl](4-methylpenyl)methane;
Bis[4-(N,N-diethylamino)-2-methylphenyl](4-methylphenyl)ethane;
4-(4-Diethylaminophenyl)triphenylmethane;
4,4'-Bis(4-diethylaminophenyl)diphenylmethane.

A useful class of triarylamines suitable for use as the host includes carbazole derivatives such as those represented by formula (G):

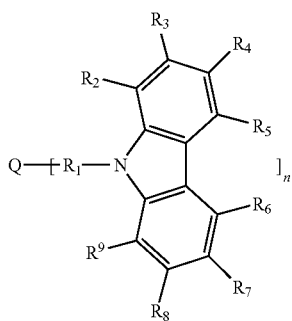

(G)

In formula (G), Q independently represents nitrogen, carbon, an aryl group, or substituted aryl group, preferably a phenyl group;

$R_1$ is preferably an aryl or substituted aryl group, and more preferably a phenyl group, substituted phenyl, biphenyl, substituted biphenyl group;

$R_2$ through $R_7$ are independently hydrogen, alkyl, phenyl or substituted phenyl group, aryl amine, carbazole, or substituted carbazole;

and n is selected from 1 to 4.

Another useful class of carbazoles satisfying structural formula (G) is represented by formula (H):

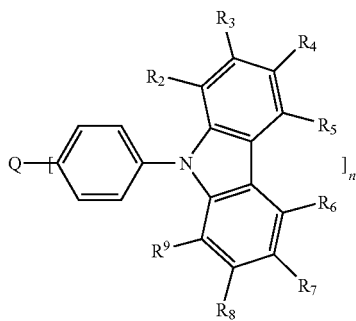

(H)

wherein:
n is an integer from 1 to 4;
Q is nitrogen, carbon, an aryl, or substituted aryl;
$R_2$ through $R_7$ are independently hydrogen, an alkyl group, phenyl or substituted phenyl, an aryl amine, a carbazole and substituted carbazole.

Illustrative of useful substituted carbazoles are the following:
4-(9H-carbazol-9-yl)-N,N-bis[4-(9H-carbazol-9-yl)phenyl]-benzenamine (TCTA);
4-(3-phenyl-9H-carbazol-9-yl)-N,N-bis[4(3-phenyl-9H-carbazol-9-yl)phenyl]-benzenamine;
9,9'-[5-[4-(9H-carbazol-9-yl)phenyl][1,1':3',1''-terphenyl]-4,4''-diyl]bis-9H-carbazole.
9,9'-(2,2'-dimethyl[1,1'-biphenyl]-4,4'-diyl)bis-9H-carbazole (CDBP);
9,9'-[1,1'-biphenyl]-4,4'-diylbis-9H-carbazole (CBP);
9,9'-(1,3-phenylene)bis-9H-carbazole (mCP);
9,9'-(1,4-phenylene)bis-9H-carbazole;
9,9',9''-(1,3,5-benzenetriyl)tris-9H-carbazole;
9,9'-(1,4-phenylene)bis[N,N,N',N'-tetraphenyl-9H-carbazole-3,6-diamine;
9-[4-(9H-carbazol-9-yl)phenyl]-N,N-diphenyl-9H-carbazol-3-amine;
9,9'-(1,4-phenylene)bis[N,N-diphenyl-9H-carbazol-3-amine;
9-[4-(9H-carbazol-9-yl)phenyl]-N,N,N',N'-tetraphenyl-9H-carbazole-3,6-diamine.

The above classes of hosts suitable for phosphorescent LELs can also be used as hosts in fluorescent LELs as well.

Suitable phosphorescent dopants for use in a phosphorescent LEL can be selected from the phosphorescent materials described by formula (J) below:

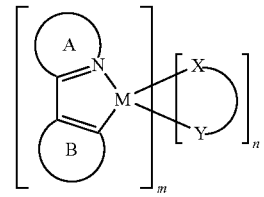

(J)

wherein:
A is a substituted or unsubstituted heterocyclic ring containing at least one nitrogen atom;
B is a substituted or unsubstituted aromatic or heteroaromatic ring, or ring containing a vinyl carbon bonded to M;
X—Y is an anionic bidentate ligand;
m is an integer from 1 to 3 and
n in an integer from 0 to 2 such that m+n=3 for M=Rh or Ir; or
m is an integer from 1 to 2 and n in an integer from 0 to 1 such that m+n=2 for M=Pt or Pd.

Compounds according to formula (J) can be referred to as C,N— (or C^N—) cyclometallated complexes to indicate that the central metal atom is contained in a cyclic unit formed by bonding the metal atom to carbon and nitrogen atoms of one or more ligands. Examples of heterocyclic ring A in formula (J) include substituted or unsubstituted pyridine, quinoline, isoquinoline, pyrimidine, indole, indazole, thiazole, and oxazole rings. Examples of ring B in formula (J) include substituted or unsubstituted phenyl, napthyl, thienyl, benzothienyl, furanyl rings. Ring B in formula (J) can also be a N-containing ring such as pyridine, with the provision that the N-containing ring bonds to M through a C atom as shown in formula (J) and not the N atom.

An example of a tris-C,N-cyclometallated complex according to formula (J) with m=3 and n=0 is tris(2-phenyl-pyridinato-N,$C^{2'}$-)Iridium (III), shown below in stereodiagrams as facial (fac-) or meridional (mer-) isomers.

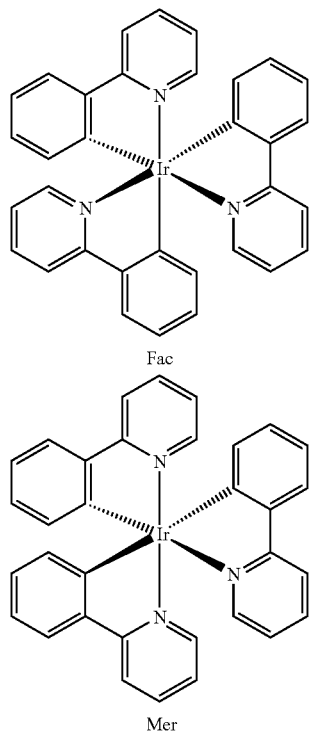

Fac

Mer

Generally, facial isomers are preferred since they are often found to have higher phosphorescent quantum yields than the meridional isomers. Additional examples of tris-C,N-cyclometallated phosphorescent materials according to formula (J) are tris(2-(4'-methylphenyl)pyridinato-N,$C^{2'}$)Iridium(III), tris(3-phenylisoquinolino-N,$C^{2'}$)Iridium(III), tris(2-phenylquinolinato-N,$C^{2'}$)Iridium(III), tris(1-phenylisoquinolinato-N,$C^{2'}$)Iridium(III), tris(1-(4'-methylphenyl)isoquinolinato-N,$C^{2'}$)Iridium(III), tris(2-(4',6'-diflourophenyl)-pyridinato-N,$C^{2'}$)Iridium(III), tris(2-((5'-phenyl)-phenyl)pyridinato-N,$C^{2'}$)Iridium(III), tris(2-(2'-benzothienyl)pyridinato-N,$C^{3'}$)Iridium(III), tris(2-phenyl-3,3'dimethyl)indolato-N,$C^{2'}$)Ir(III), tris(1-phenyl-1H-indazolato-N,$C^{2'}$)Ir(III).

Of these, tris(1-phenylisoquinoline)iridium(III) (also referred to as Ir(piq)$_3$) and tris(2-phenylpyridine) iridium (also referred to as Ir(ppy)$_3$) are particularly suitable for this invention.

Tris-C,N-cyclometallated phosphorescent materials also include compounds according to formula (J) wherein the monoanionic bidentate ligand X—Y is another C,N-cyclometallating ligand. Examples include bis(1-phenylisoquinolinato-N,$C^{2'}$)(2-phenylpyridinato-N,$C^{2'}$)Iridium(III) and bis (2-phenylpyridinato-N,$C^{2'}$)(1-phenylisoquinolinato-N,$C^{2'}$) Iridium(III). Synthesis of such tris-C,N-cyclometallated complexes containing two different C,N-cyclometallating ligands can be conveniently synthesized by the following steps. First, a bis-C,N-cyclometallated diiridium dihalide complex (or analogous dirhodium complex) is made according to the method of Nonoyama (*Bull. Chem. Soc. Jpn.*, 47, 767 (1974)). Secondly, a zinc complex of the second, dissimilar C,N-cyclometallating ligand is prepared by reaction of a zinc halide with a lithium complex or Grignard reagent of the cyclometallating ligand. Third, the formed zinc complex of the second C,N-cyclometallating ligand is reacted with the previously obtained bis-C,N-cyclometallated diiridium dihalide complex to form a tris-C,N-cyclometallated complex containing the two different C,N-cyclometallating ligands. Desirably, the obtained tris-C,N-cyclometallated complex containing the two different C,N-cyclometallating ligands can be converted to an isomer wherein the C atoms bonded to the metal (e.g. Ir) are all mutually cis by heating in a suitable solvent such as dimethyl sulfoxide.

Suitable phosphorescent materials according to formula (J) can in addition to the C,N-cyclometallating ligand(s) also contain monoanionic bidentate ligand(s) X—Y that are not C,N-cyclometallating. Common examples are beta-diketonates such as acetylacetonate, and Schiff bases such as picolinate.

Examples of such mixed ligand complexes according to formula (J) include bis(2-phenylpyridinato-N,$C^{2'}$)Iridium (III)(acetylacetonate), bis(2-(2'-benzothienyl)pyridinato-N, $C^{3'}$)Iridium(III)(acetylacetonate), and bis(2-(4',6'-diflourophenyl)-pyridinato-N,$C^{2'}$)Iridium(III)(picolinate).

Other important phosphorescent materials according to formula (J) include C,N-cyclometallated Pt(II) complexes such as cis-bis(2-phenylpyridinato-N,$C^{2'}$)platinum(II), cis-bis(2-(2'-thienyl)pyridinato-N,$C^{3'}$) platinum(II), cis-bis(2-(2'-thienyl)quinolinato-N,$C^{5'}$) platinum(II), or (2-(4',6'-diflourophenyl)pyridinato-N,$C^{2'}$)platinum(II) (acetylacetonate).

The emission wavelengths (color) of C,N-cyclometallated phosphorescent materials according to formula (J) are governed principally by the lowest energy optical transition of the complex and hence by the choice of the C,N-cyclometallating ligand. For example, 2-phenyl-pyridinato-N,$C^{2'}$ complexes are typically green emissive while 1-phenyl-isoquinolinolato-N,$C^{2'}$ complexes are typically red emissive. In the case of complexes having more than one C,N-cyclometallating ligand, the emission will be that of the ligand having the property of longest wavelength emission. Emission wavelengths can be further shifted by the effects of substituent groups on the C,N-cyclometallating ligands. For example, substitution of electron donating groups at appropriate positions on the N-containing ring A or electron accepting groups on the C-containing ring B tend to blue-shift the emission relative to the unsubstituted C,N-cyclometallated ligand complex. Selecting a monodentate anionic ligand X,Y in formula (J) having more electron accepting properties also tends to blue-shift the emission of a C,N-cyclometallated ligand complex. Examples of complexes having both monoanionic bidentate ligands possessing electron accepting properties and electron accepting substituent groups on the C-containing ring B include bis(2-(4',6'-difluorophenyl)-pyridinato-N,$C^{2'}$)iridium(III)(picolinate) and bis(2-(4',6'-difluorophenyl)-pyridinato-N,$C^{2'}$)iridium(III)(tetrakis(1-pyrazolyl)borate).

The central metal atom in phosphorescent materials according to formula (J) can be Rh or Ir (m+n=3) and Pd or Pt (m+n=2). Preferred metal atoms are Ir and Pt since they tend to give higher phosphorescent quantum efficiencies according to the stronger spin-orbit coupling interactions generally obtained with elements in the third transition series.

In addition to bidentate C,N-cyclometallating complexes represented by formula (J), many suitable phosphorescent materials contain multidentate C,N-cyclometallating ligands. Phosphorescent materials having tridentate ligands suitable for use in the present invention are disclosed in U.S. Pat. No. 6,824,895. Phosphorescent materials having tetradentate ligands suitable for use in the present invention are described by the following formulae:

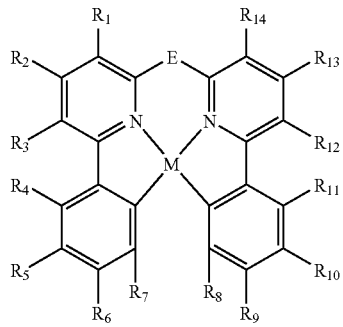
(K)

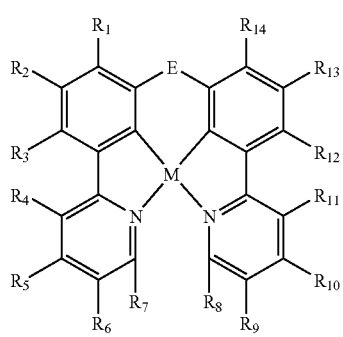
(L)

wherein:

M is Pt or Pd;

$R^1$-$R^7$ represent hydrogen or independently selected substituents, provided that $R^1$ and $R^2$, $R^2$ and $R^3$, $R^3$ and $R^4$, $R^4$ and $R^5$, $R^5$ and $R^6$, as well as $R^6$ and $R^7$ can join to form a ring group;

$R^8$-$R^{14}$ represent hydrogen or independently selected substituents, provided that $R^8$ and $R^9$, $R^9$ and $R^{10}$, $R^{10}$ and $R^{11}$, $R^{11}$ and $R^{12}$, $R^{12}$ and $R^{13}$, as well as $R^{13}$ and $R^{14}$, can join to form a ring group;

E represents a bridging group selected from the following:

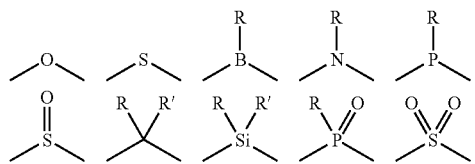

wherein:

R and R' represent hydrogen or independently selected substituents; provided R and R' can combine to form a ring group.

One desirable tetradentate C,N-cyclometallated phosphorescent material suitable for use in as the phosphorescent dopant is represented by the following formula:

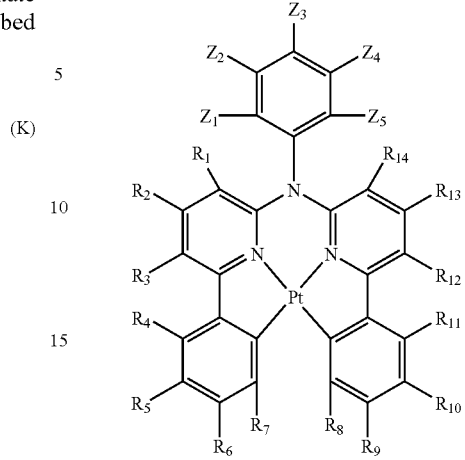
(M)

wherein:

$R^1$-$R^7$ represent hydrogen or independently selected substituents, provided that $R^1$ and $R^2$, $R^2$ and $R^3$, $R^3$ and $R^4$, $R^4$ and $R^5$, $R^5$ and $R^6$, as well as $R^6$ and $R^7$ can combine to form a ring group;

$R^8$-$R^{14}$ represent hydrogen or independently selected substituents, provided that $R^8$ and $R^9$, $R^9$ and $R^{10}$, $R^{10}$ and $R^{11}$, $R^{11}$ and $R^{12}$, $R^{12}$ and $R^{13}$, as well as $R^{13}$ and $R^{14}$ can combine to form a ring group;

$Z^1$-$Z^5$ represent hydrogen or independently selected substituents, provided that $Z^1$ and $Z^2$, $Z^2$ and $Z^3$, $Z^3$ and $Z^4$, as well as $Z^4$ and $Z^5$ can combine to form a ring group.

Specific examples of phosphorescent materials having tetradentate C,N-cyclometallating ligands suitable for use in the present invention include compounds (M-1), (M-2) and (M-3) represented below.

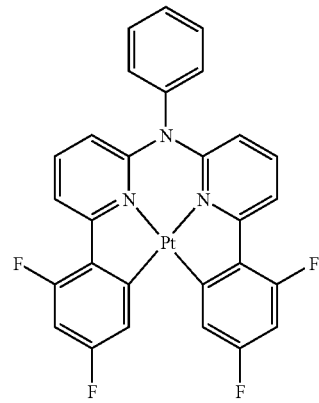
(M-1)

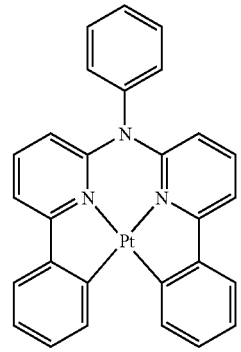
(M-2)

(M-3)

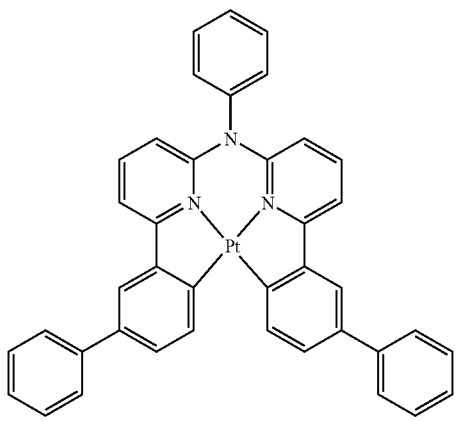

Phosphorescent materials having tetradentate C,N-cyclometallating ligands can be synthesized by reacting the tetradentate C,N-cyclometallating ligand with a salt of the desired metal, such as $K_2PtCl_4$, in a proper organic solvent such as glacial acetic acid to form the phosphorescent material having tetradentate C,N-cyclometallating ligands. A tetraalkylammonium salt such as tetrabutylammonium chloride can be used as a phase transfer catalyst to accelerate the reaction.

Other phosphorescent materials that do not involve C,N-cyclometallating ligands are known. Phosphorescent complexes of Pt(II), Ir(I), and Rh(I) with maleonitriledithiolate have been reported (Johnson et al., *J. Am Chem. Soc.*, 105, 1795 (1983)). Re(I) tricarbonyl diimine complexes are also known to be highly phosphorescent (Wrighton and Morse, *J. Am. Chem. Soc.*, 96, 998 (1974); Stufkens, *Comments Inorg. Chem.*, 13, 359 (1992); Yam, *Chem. Commun.*, 789 (2001)). Os(II) complexes containing a combination of ligands including cyano ligands and bipyridyl or phenanthroline ligands have also been demonstrated in a polymer OLED (Ma et al., *Synthetic Metals*, 94, 245 (1998)).

Porphyrin complexes such as 2,3,7,8,12,13,17,18-octaethyl-21H, 23H-porphine platinum(II) are also useful phosphorescent dopant.

Still other examples of useful phosphorescent materials include coordination complexes of the trivalent lanthanides such as $Tb^{3+}$ and $Eu^{3+}$ (Kido et al., *Chem. Lett.*, 657 (1990); *J. Alloys and Compounds*, 192, 30 (1993); *Jpn. J. AppL Phys.*, 35, L394 (1996) and *Appl. Phys. Lett.*, 65, 2124 (1994)).

The phosphorescent dopant in a phosphorescent LEL is typically present in an amount of from 1 to 20% by volume of the LEL, and conveniently from 2 to 8% by volume of the LEL. In some embodiments, the phosphorescent dopant(s) can be attached to one or more host materials. The host materials can further be polymers. The phosphorescent dopant in the first phosphorescent light-emitting layer is selected from green and red phosphorescent materials.

The thickness of a phosphorescent LEL is greater than 0.5 nm, preferably, in the range of from 1.0 nm to 40 nm.

b) Fluorescent Light Emitting Layers

Although the term "fluorescent" is commonly used to describe any light-emitting material, in this case it refers to a material that emits light from a singlet excited state. Fluorescent materials can be used in the same layer as the phosphorescent material, in adjacent layers, in adjacent pixels, or any combination. Care must be taken not to select materials that will adversely affect the performance of the phosphorescent materials of this invention. One skilled in the art will understand that concentrations and triplet energies of materials in the same layer as the phosphorescent material or in an adjacent layer must be appropriately set so as to prevent unwanted quenching of the phosphorescence.

Typically, a fluorescent LEL includes at least one host and at least one fluorescent dopant. The host can be a hole-transporting material or any of the suitable hosts for phosphorescent dopants as defined above or can be an electron-transporting material as defined below.

The dopant is typically chosen from highly fluorescent dyes, e.g., transition metal complexes as described in WO 98/55561 A1, WO 00/18851 A1, WO 00/57676 A1, and WO 00/70655.

Useful fluorescent dopants include, but are not limited to, derivatives of anthracene, tetracene, xanthene, perylene, phenylene, dicyanomethylenepyran compounds, thiopyran compounds, polymethine compounds, pyrylium and thiapyrylium compounds, arylpyrene compounds, arylenevinylene compounds, periflanthene derivatives, indenoperylene derivatives, bis(azinyl)amine boron compounds, bis(azinyl)methane boron compounds, distryrylbenzene derivatives, distyrylbiphenyl derivatives, distyrylamine derivatives and carbostyryl compounds.

Some fluorescent emitting materials include, but are not limited to, derivatives of anthracene, tetracene, xanthene, perylene, rubrene, coumarin, rhodamine, and quinacridone, dicyanomethylenepyran compounds, thiopyran compounds, polymethine compounds, pyrylium and thiapyrylium compounds, fluorene derivatives, periflanthene derivatives, indenoperylene derivatives, bis(azinyl)amine boron compounds, bis(azinyl)methane compounds (as described in U.S. Pat. No. 5,121,029) and carbostyryl compounds. Illustrative examples of useful materials include, but are not limited to, the following:

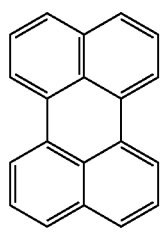

FD-1

-continued
FD-2
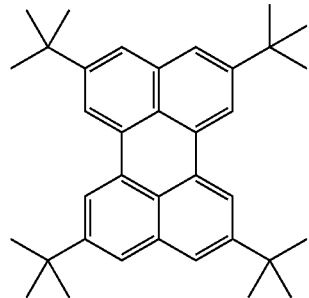
FD-3
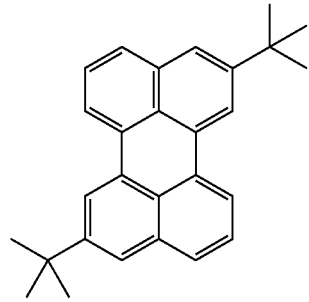
FD-4
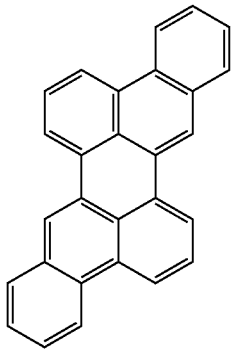
FD-5
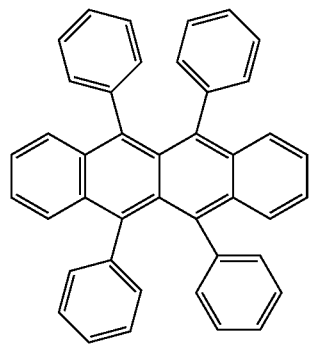
FD-6
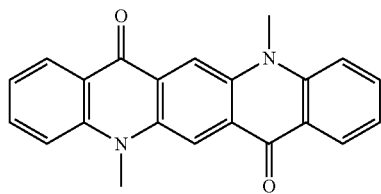

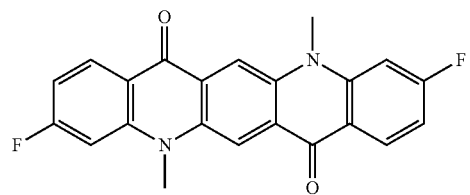
FD-7
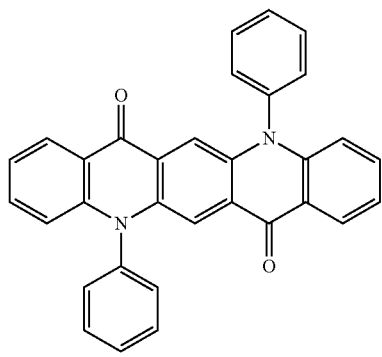
FD-8
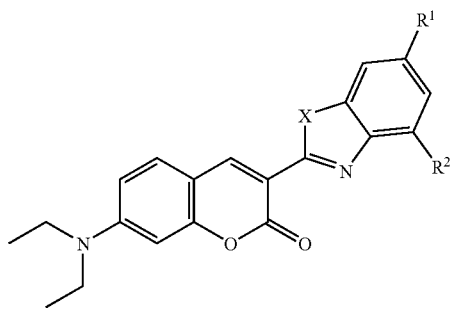
|       | X | R1     | R2     |
|-------|---|--------|--------|
| FD-9  | O | H      | H      |
| FD-10 | O | H      | Methyl |
| FD-11 | O | Methyl | H      |
| FD-12 | O | Methyl | Methyl |
| FD-13 | O | H      | t-butyl |
| FD-14 | O | t-butyl | H     |
| FD-15 | O | t-butyl | t-butyl |
| FD-16 | S | H      | H      |
| FD-17 | S | H      | Methyl |
| FD-18 | S | Methyl | H      |
| FD-19 | S | Methyl | Methyl |
| FD-20 | S | H      | t-butyl |
| FD-21 | S | t-butyl | H     |
| FD-22 | S | t-butyl | t-butyl |

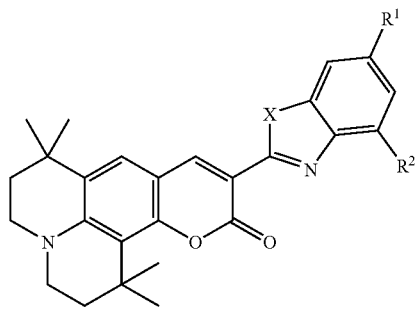
| | X | R1 | R2 |
|---|---|---|---|
| FD-13 | O | H | H |
| FD-24 | O | H | Methyl |
| FD-25 | O | Methyl | H |
| FD-26 | O | Methyl | Methyl |
| FD-27 | O | H | t-butyl |
| FD-28 | O | t-butyl | H |
| FD-29 | O | t-butyl | t-butyl |
| FD-30 | S | H | H |
| FD-31 | S | H | Methyl |
| FD-32 | S | Methyl | H |
| FD-33 | S | Methyl | Methyl |
| FD-34 | S | H | t-butyl |
| FD-35 | S | t-butyl | H |
| FD-36 | S | t-butyl | t-butyl |
| | R |
|---|---|
| FD-37 | phenyl |
| FD-38 | methyl |
| FD-39 | t-butyl |
| FD-40 | mesityl |
| | R |
|---|---|
| FD-41 | phenyl |
| FD-42 | methyl |

-continued
| | |
|---|---|
| FD-43 | t-butyl |
| FD-44 | mesityl |
FD-45
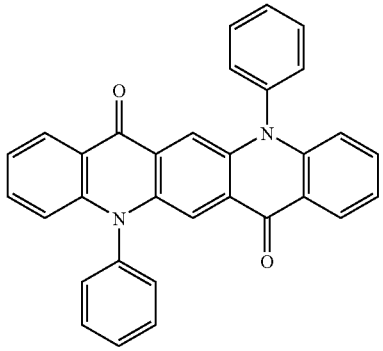
FD-46
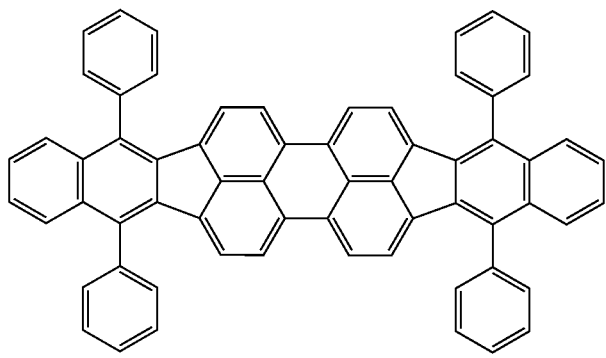
FD-47
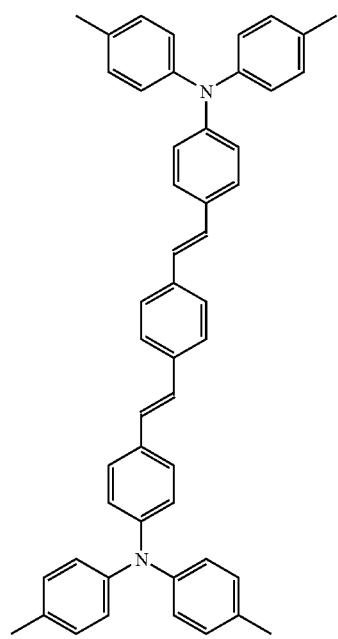

-continued
FD-48
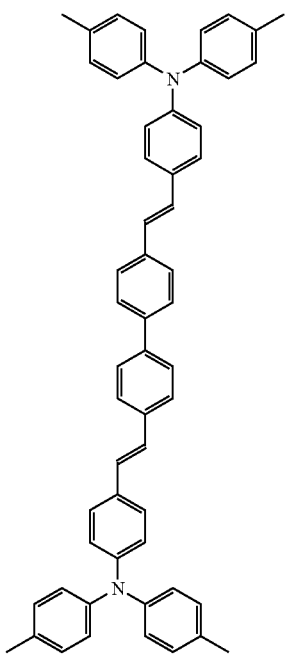
FD-49
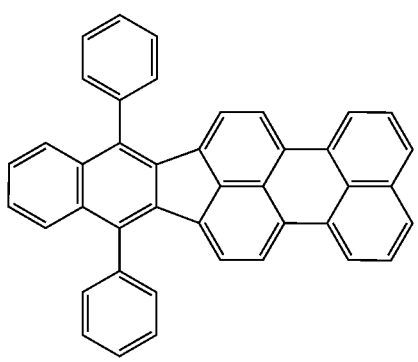
FD-50
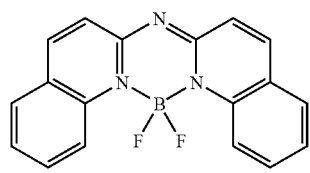
FD-51
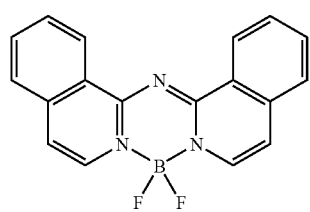

FD-52
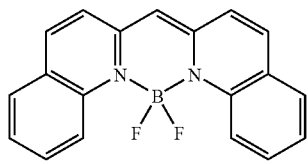
FD-53
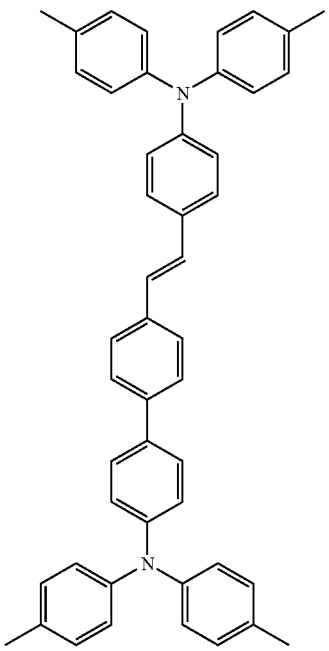
FD-54
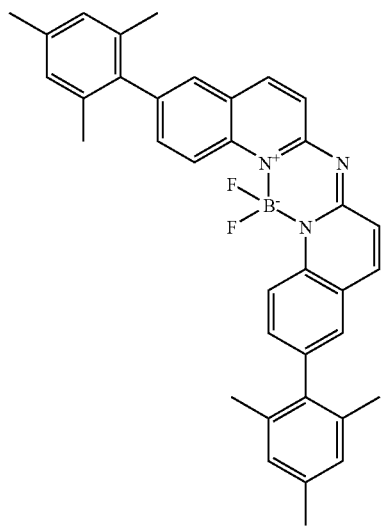
FD-55
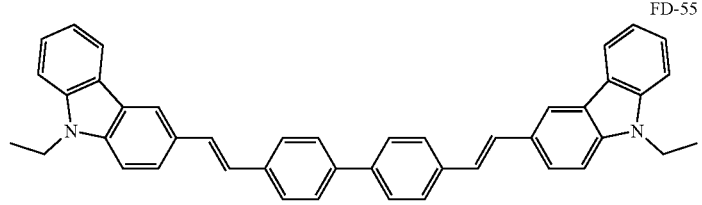

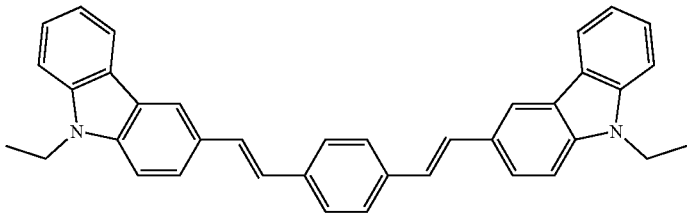

FD-56

Preferred fluorescent blue dopants can be found in Chen, Shi, and Tang, "Recent Developments in Molecular Organic Electroluminescent Materials," *Macromol. Symp.* 125, 1 (1997) and the references cited therein; Hung and Chen, "Recent Progress of Molecular Organic Electroluminescent Materials and Devices," *Mat. Sci. and Eng. R*39, 143 (2002) and the references cited therein.

A particularly preferred class of blue-emitting fluorescent dopants is represented by Formula (N), known as a bis(azinyl0amine borane complex, and is described in U.S. Pat. No. 6,661,023.

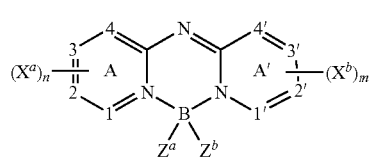

Formula (N)

wherein:
A and A' represent independent azine ring systems corresponding to 6-membered aromatic ring systems containing at least one nitrogen;
each $X^a$ and $X^b$ is an independently selected substituent, two of which can join to form a fused ring to A or A';
m and n are independently 0 to 4;
$Z^a$ and $Z^b$ are independently selected substituents; and
1, 2, 3, 4, 1', 2', 3', and 4' are independently selected as either carbon or nitrogen atoms.

Desirably, the azine rings are either quinolinyl or isoquinolinyl rings such that 1, 2, 3, 4, 1', 2', 3', and 4' are all carbon; m and n are equal to or greater than 2; and $X^a$ and $X^b$ represent at least two carbon substituents which join to form an aromatic ring. Desirably, $Z^a$ and $Z^b$ are fluorine atoms.

Preferred embodiments further include devices where the two fused ring systems are quinoline or isoquinoline systems; the aryl or heterocyclic substituent is a phenyl group; there are present at least two $X^a$ groups and two $X^b$ groups which join to form a 6-6 fused ring, the fused ring systems are fused at the 1-2, 3-4, 1'-2', or 3'-4' positions, respectively; one or both of the fused rings is substituted by a phenyl group; and where the dopant is depicted in Formulae (N-a), (N-b), or (N-c).

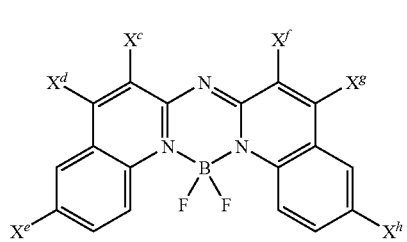

Formula (N-a)

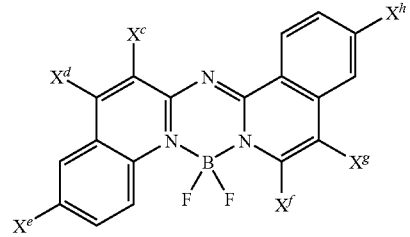

Formula (N-b)

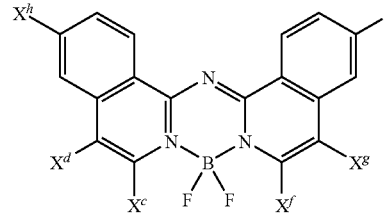

Formula (N-c)

wherein:
each $X^c$, $X^d$, $X^e$, $X^f$, $X^g$, and $X^h$ is hydrogen or an independently selected substituent, one of which must be an aryl or heterocyclic group.

Desirably, the azine rings are either quinolinyl or isoquinolinyl rings such that 1, 2, 3, 4, 1', 2', 3', and 4' are all carbon; m and n are equal to or greater than 2; and $X^a$ and $X^b$ represent at least two carbon substituents which join to form an aromatic ring, and one is an aryl or substituted aryl group. Desirably, $Z^a$ and $Z^b$ are fluorine atoms.

Of these, compound FD-54 is particularly useful.

Coumarins represent a useful class of green-emitting dopants as described by Tang et al. in U.S. Pat. Nos. 4,769,292 and 6,020,078. Green dopants or light-emitting materials can be coated as 0.01 to 50% by weight into the host material, but typically coated as 0.01 to 30% and more typically coated as 0.01 to 15% by weight into the host material. Examples of useful green-emitting coumarins include C545T and C545TB. Quinacridones represent another useful class of green-emitting dopants. Useful quinacridones are described in U.S. Pat. No. 5,593,788 and JP 09-13026A.

Examples of particularly useful green-emitting quinacridones are FD-7 and FD-8.

Formula (N-d) below represents another class of green-emitting dopants useful in the invention.

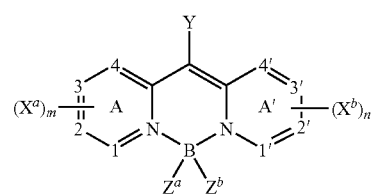

Formula (N-d)

wherein:

A and A' represent independent azine ring systems corresponding to 6-membered aromatic ring systems containing at least one nitrogen;

each $X^a$ and $X^b$ is an independently selected substituent, two of which can join to form a fused ring to A or A';

m and n are independently 0 to 4;

Y is H or a substituent;

$Z^a$ and $Z^b$ are independently selected substituents; and 1, 2, 3, 4, 1', 2', 3', and 4' are independently selected as either carbon or nitrogen atoms.

In the device, 1, 2, 3, 4, 1', 2', 3', and 4' are conveniently all carbon atoms. The device can contain at least one or both of ring A or A' that contains substituents joined to form a fused ring. In one useful embodiment, there is present at least one $X^a$ or $X^b$ group selected from the group consisting of halide and alkyl, aryl, alkoxy, and aryloxy groups. In another embodiment, there is present a $Z^a$ and $Z^b$ group independently selected from the group consisting of fluorine and alkyl, aryl, alkoxy and aryloxy groups. A desirable embodiment is where $Z^a$ and $Z^b$ are F. Y is suitably hydrogen or a substituent such as an alkyl, aryl, or heterocyclic group.

The emission wavelength of these compounds can be adjusted to some extent by appropriate substitution around the central bis(azinyl)methene boron group to meet a color aim, namely green. Some examples of useful material are FD-50, FD-51 and FD-52.

Naphthacenes and derivatives thereof also represent a useful class of emitting dopants, which can also be used as stabilizers. These dopant materials can be coated as 0.01 to 50% by weight into the host material, but typically coated as 0.01 to 30% and more typically coated as 0.01 to 15% by weight into the host material. Naphthacene derivative YD-1 (t-BuDPN) below, is an example of a dopant material used as a stabilizer.

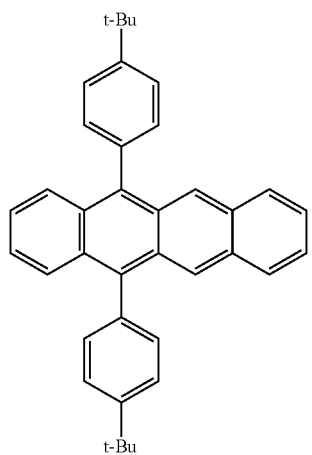

YD-1

Some examples of this class of materials are also suitable as host materials as well as dopants. For example, see U.S. Pat. No. 6,773,832 or 6,720,092. A specific example of this would be rubrene (FD-5).

Another class of useful dopants are perylene derivatives; for example see U.S. Pat. No. 6,689,493. A specific examples is FD-46.

Metal complexes of 8-hydroxyquinoline and similar derivatives (Formula O) constitute one class of useful non-electroluminescent host compounds capable of supporting electroluminescence, and are particularly suitable for light emission of wavelengths longer than 500 nm, e.g., green, yellow, orange, and red.

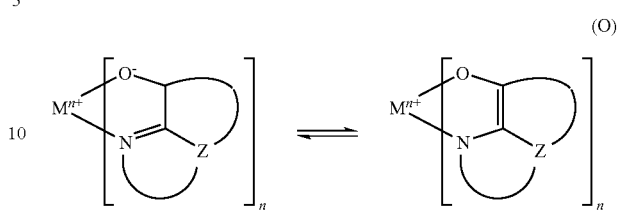

(O)

wherein:

M represents a metal;

n is an integer of from 1 to 4; and

Z independently in each occurrence represents the atoms completing a nucleus having at least two fused aromatic rings.

From the foregoing it is apparent that the metal can be monovalent, divalent, trivalent, or tetravalent metal. The metal can, for example, be an alkali metal, such as lithium, sodium, or potassium; an alkaline earth metal, such as magnesium or calcium; an earth metal, such as aluminum or gallium, or a transition metal such as zinc or zirconium. Generally any monovalent, divalent, trivalent, or tetravalent metal known to be a useful chelating metal can be employed.

Z completes a heterocyclic nucleus containing at least two fused aromatic rings, at least one of which is an azole or azine ring. Additional rings, including both aliphatic and aromatic rings, can be fused with the two required rings, if required. To avoid adding molecular bulk without improving on function the number of ring atoms is usually maintained at 18 or less.

Illustrative of useful chelated oxinoid compounds are the following:

O-1: Aluminum trisoxine[alias, tris(8-quinolinolato)aluminum(III)]

O-2: Magnesium bisoxine [alias, bis(8-quinolinolato)magnesium(II)]

O-3: Bis[benzo{f}-8-quinolinolato]zinc(II)

O-4: Bis(2-methyl-8-quinolinolato)aluminum(III)-y-oxo-bis(2-methyl-8-quinolinolato) aluminum(III)

O-5: Indium trisoxine[alias, tris(8-quinolinolato)indium]

O-6: Aluminum tris(5-methyloxine)[alias, tris(5-methyl-8-quinolinolato) aluminum(III)]

O-7: Lithium oxine[alias, (8-quinolinolato)lithium(I)]

O-8: Gallium oxine[alias, tris(8-quinolinolato)gallium (III)]

O-9: Zirconium oxine[alias, tetra(8-quinolinolato)zirconium(IV)]

O-10: Bis(2-methyl-8-quinolinato)-4-phenylphenolatoaluminum(III)

Anthracene derivatives according to formula (P) are also useful host materials in the LEL:

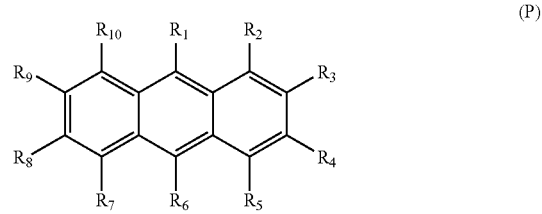

(P)

wherein:

$R_1$-$R_{10}$ are independently chosen from hydrogen, alkyl groups from 1-24 carbon atoms or aromatic groups from 6-24 carbon atoms. Particularly preferred are compounds where $R_1$ and $R_6$ are phenyl, biphenyl or napthyl, $R_3$ is phenyl, substituted phenyl or napthyl and $R_2$, $R_4$, $R_5$, $R_7$-$R_{10}$ are all hydrogen. Such anthracene hosts are known to have excellent electron transporting properties.

Particularly desirable are derivatives of 9,10-di-(2-naphthyl)anthracene. Illustrative examples include 9,10-di-(2-naphthyl)anthracene (ADN) and 2-t-butyl-9,10-di-(2-naphthyl)anthracene (TBADN). Other anthracene derivatives can be useful as an non-electroluminescent compound in the LEL, such as diphenylanthracene and its derivatives, as described in U.S. Pat. No. 5,927,247. Styrylarylene derivatives as described in U.S. Pat. No. 5,121,029 and JP 08333569 are also useful non-electroluminescent materials. For example, 9,10-bis[4-(2,2-diphenylethenyl)phenyl]anthracene, 4,4'-Bis(2,2-diphenylethenyl)-1,1'-biphenyl (DPVBi) and phenylanthracene derivatives as described in EP 681,019 are useful non-electroluminescent materials.

Some illustrative examples of suitable anthracenes are:

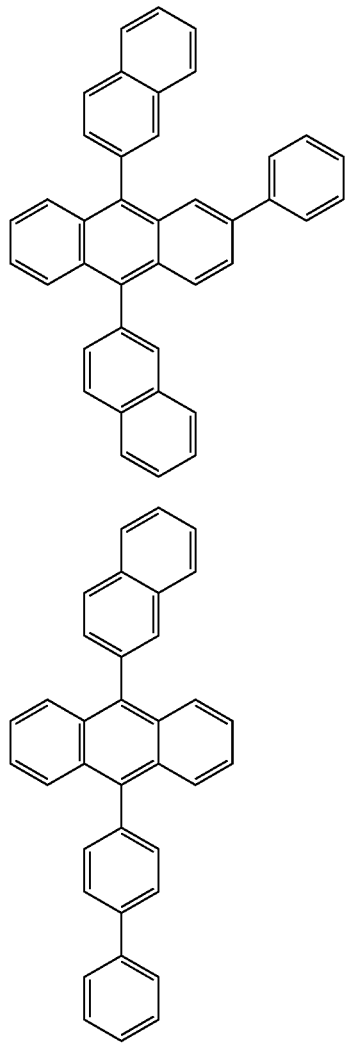

(P-1)

(P-2)

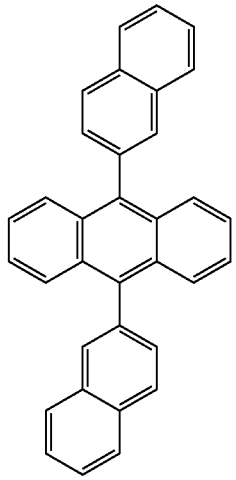

(P-3)

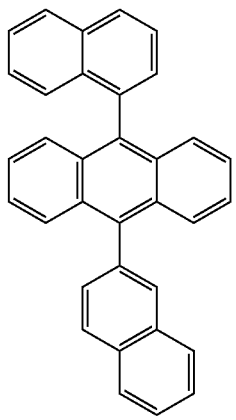

(P-4)

Spacer Layer

Spacer layers, when present, are located in direct contact to a LEL. They can be located on either the anode or cathode, or even both sides of the LEL. They typically do not contain any light-emissive dopants. One or more materials can be used and could be either a hole-transporting material as defined above or an electron-transporting material as defined below. If located next to a phosphorescent LEL, the material in the spacer layer should have higher triplet energy than that of the phosphorescent dopant in the LEL. Most desirably, the material in the spacer layer will be the same as used as the host in the adjacent LEL. Thus, any of the host materials described as also suitable for use in a spacer layer. The spacer layer should be thin; at least 0.1 nm, but preferably in the range of from 1.0 nm to 20 nm.

Hole-Blocking Layer (HBL)

When a LEL containing a phosphorescent emitter is present, it is desirable to locate a hole-blocking layer 135 between the electron-transporting layer 136 and the light-emitting layer 134 to help confine the excitons and recombination events to the LEL. In this case, there should be an energy barrier for hole migration from co-hosts into the hole-blocking layer, while electrons should pass readily from the hole-blocking layer into the light-emitting layer comprising co-host materials and a phosphorescent emitter. It is further desirable that the triplet energy of the hole-blocking material be greater than that of the phosphorescent material. Suitable hole-blocking materials are described in WO 00/70655A2, WO 01/41512 and WO 01/93642 A1. Two examples of useful hole-blocking materials are bathocuproine (BCP) and bis(2-methyl-8-quinolinolato)(4-phenylphenolato)aluminum(III) (BAlq). Metal complexes other than BAlq are also known to block holes and excitons as described in U.S. Patent Application Publication No. 2003/0068528. When a hole-blocking layer is used, its thickness can be between 2 and 100 nm and suitably between 5 and 10 nm.

Electron Transporting Layer

In some embodiments, the electron-transporting layer 136 can contain the cyclobutene compound or can be a mixture of the cyclobutene compound with other appropriate materials. As described previously, in one desirable embodiment, the electron-transporting layer includes polycyclic aromatic compound such as a fluoranthene derivative or a 9,10-diarylanthracene derivative. In particular, fluoranthene hydrocarbon derivatives with aromatic groups in the 7,10-positions are particularly desirable. In other embodiments, the ETL contains both the cyclobutene compound and a polycyclic aromatic compound. In a further embodiment, the electron-transporting layer also contains at least one material chosen from alkali metals, alkali metal compounds, alkaline earth metals, or alkaline earth metal compounds, or combinations thereof.

In addition to any of the electron-transporting materials previously described, any other materials known to be suitable for use in the ETL can be used. Included are, but are not limited to, chelated oxinoid compounds, anthracene derivatives, pyridine-based materials, imidazoles, oxazoles, thiazoles and their derivatives, polybenzobisazoles, cyano-containing polymers and perfluorinated materials. Other electron-transporting materials include various butadiene derivatives as disclosed in U.S. Pat. No. 4,356,429 and various heterocyclic optical brighteners as described in U.S. Pat. No. 4,539,507.

A preferred class of benzazoles is described by Shi et al. in U.S. Pat. Nos. 5,645,948 and 5,766,779. Such compounds are represented by structural formula (Q):

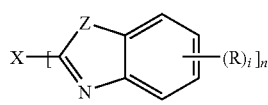
(Q)

In formula (Q), n is selected from 2 to 8 and i is selected from 1-5;

Z is independently O, NR or S;

R is individually hydrogen; alkyl of from 1 to 24 carbon atoms, for example, propyl, t-butyl, heptyl, and the like; aryl or hetero-atom substituted aryl of from 5 to 20 carbon atoms, for example, phenyl and naphthyl, furyl, thienyl, pyridyl, quinolinyl and other heterocyclic systems; or halo such as chloro, fluoro; or atoms necessary to complete a fused aromatic ring; and X is a linkage unit consisting of carbon, alkyl, aryl, substituted alkyl, or substituted aryl, which conjugately or unconjugately connects the multiple benzazoles together.

An example of a useful benzazole is 2,2',2"-(1,3,5-phenylene)tris[1-phenyl-1H-benzimidazole] (TPBI) represented by a formula (Q-1) shown below:

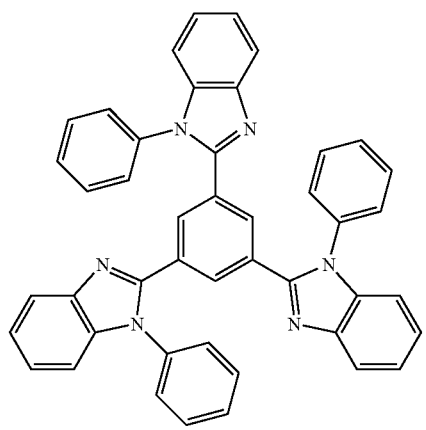
(Q-1)

Another suitable class of the electron-transporting materials includes various substituted phenanthrolines as represented by formula (R).

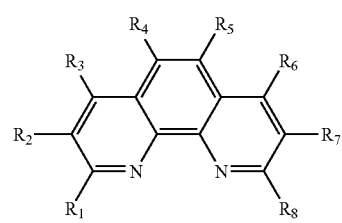
(R)

In formula (R), $R_1$-$R_8$ are independently hydrogen, alkyl group, aryl or substituted aryl group, and at least one of $R_1$-$R_8$ is aryl group or substituted aryl group.

Specific examples of the phenanthrolines useful in the EIL are 2,9-dimethyl-4,7-diphenyl-phenanthroline (BCP) (see formula (R-1)) and 4,7-diphenyl-1,10-phenanthroline (Bphen) (see formula (R-2)).

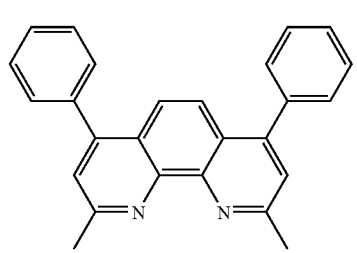
(R-1)

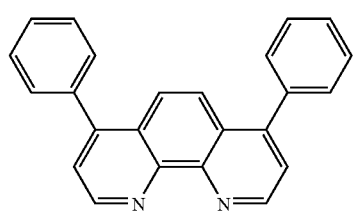
(R-2)

Suitable triarylboranes that function as an electron-transporting material can be selected from compounds having the chemical formula (S):

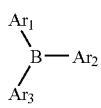
(S)

wherein:

Ar$_1$ to Ar$_3$ are independently an aromatic hydrocarbocyclic group or an aromatic heterocyclic group which can have a substituent. It is preferable that compounds having the above structure are selected from formula (S-1):

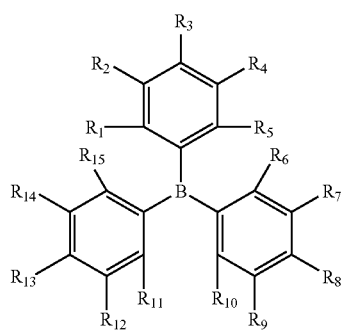
(S-1)

wherein:

R$_1$-R$_{15}$ are independently hydrogen, fluoro, cyano, trifluoromethyl, sulfonyl, alkyl, aryl or substituted aryl group.

Specific representative embodiments of the triarylboranes include:

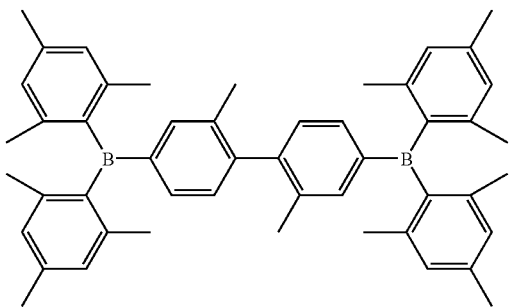
(S-1)

(S-2)

(S-3)

The electron-transporting material can also be selected from substituted 1,3,4-oxadiazoles of formula (T):

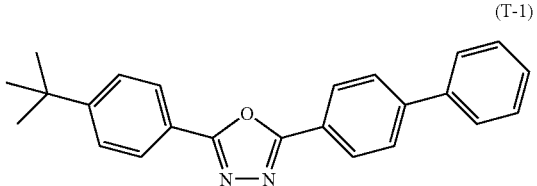
(T)

wherein:

R$_1$ and R$_2$ are individually hydrogen; alkyl of from 1 to 24 carbon atoms, for example, propyl, t-butyl, heptyl, and the like; aryl or hetero-atom substituted aryl of from 5 to 20 carbon atoms, for example, phenyl and naphthyl, furyl, thienyl, pyridyl, quinolinyl and other heterocyclic systems; or halo such as chloro, fluoro; or atoms necessary to complete a fused aromatic ring.

Illustrative of the useful substituted oxadiazoles are the following:

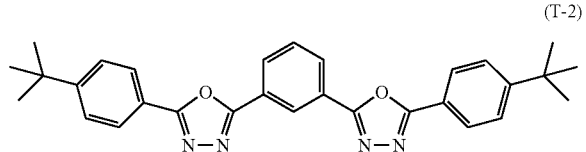
(T-1)

(T-2)

The electron-transporting material can also be selected from substituted 1,2,4-triazoles according to formula (U):

(U)

wherein:

R$_1$, R$_2$ and R$_3$ are independently hydrogen, alkyl group, aryl or substituted aryl group, and at least one of R$_1$-R$_3$ is aryl group or substituted aryl group. An example of a useful triazole is 3-phenyl-4-(1-naphtyl)-5-phenyl-1,2,4-triazole represented by formula (U-1):

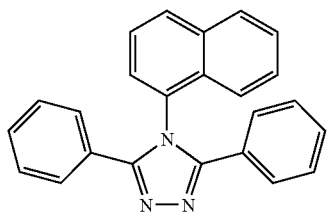

(U-1)

The electron-transporting material can also be selected from substituted 1,3,5-triazines. Examples of suitable materials are:
2,4,6-tris(diphenylamino)-1,3,5-triazine;
2,4,6-tricarbazolo-1,3,5-triazine;
2,4,6-tris(N-phenyl-2-naphthylamino)-1,3,5-triazine;
2,4,6-tris(N-phenyl-1-naphthylamino)-1,3,5-triazine;
4,4',6,6'-tetraphenyl-2,2'-bi-1,3,5-triazine;
2,4,6-tris([1,1':3',1''-terphenyl]-5'-yl)-1,3,5-triazine.

In addition, any of the metal chelated oxinoid compounds including chelates of oxine itself (also commonly referred to as 8-quinolinol or 8-hydroxyquinoline) of Formula (O) useful as host materials in a LEL are also suitable for use in the ETL.

Some metal chelated oxinoid compounds having high triplet energy can be particularly useful as an electron-transporting materials. Particularly useful aluminum or gallium complex host materials with high triplet energy levels are represented by Formula (W).

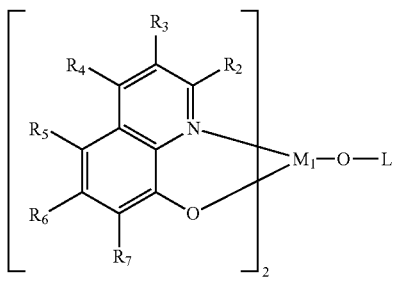

(W)

In Formula (W), $M_1$ represents Al or Ga. $R_2$-$R_7$ represent hydrogen or an independently selected substituent. Desirably, $R_2$ represents an electron-donating group. Suitably, $R_3$ and $R_4$ each independently represent hydrogen or an electron donating substituent. A preferred electron-donating group is alkyl such as methyl. Preferably, $R_5$, $R_6$, and $R_7$ each independently represent hydrogen or an electron-accepting group. Adjacent substituents, $R_2$-$R_7$, can combine to form a ring group. L is an aromatic moiety linked to the aluminum by oxygen, which can be substituted with substituent groups such that L has from 6 to 30 carbon atoms.

Illustrative of useful chelated oxinoid compounds for use in the ETL is Aluminum(III)bis(2-methyl-8-hydroxyquinoline)-4-phenylphenolate [alias, Balq].

The same anthracene derivatives according to formula (P) useful as host materials in the LEL can also be used in the ETL.

The thickness of the ETL is typically in the range of from 5 nm to 200 nm, preferably, in the range of from 10 nm to 150 nm.

Electron Injection Layer

As described previously, in some embodiments of the invention, the electron-injecting layer contains the cyclobutene compound. In some embodiments an alkali metal compound such as LiF or Li metal or an organic lithium compound such as AM-2 is located in the EIL 138. In further embodiments both an alkali metal compound and the cyclobutene compound are present in the electron-injecting layer. Likewise, is some embodiments, the EIL can be subdivided into an EIL1 (adjacent to the ETL) containing the cyclobutene compound and an EIL2 (adjacent to the cathode) containing an alkali metal or alkali metal compound. In a still further embodiment, the cyclobutene compound is present in the ETL, a phenanthroline compound as represented by formula (R), e.g. Bhen, is present in the EIL1 and an alkali metal or alkali metal compound is present in the EIL2.

Other suitable materials can also be used in the EIL. For example, the EIL can be an n-type doped layer containing at least one electron-transporting material as a host and at least one n-type dopant. The dopant is capable of reducing the host by charge transfer. The term "n-type doped layer" means that this layer has semiconducting properties after doping, and the electrical current through this layer is substantially carried by the electrons.

The host in the EIL can be an electron-transporting material capable of supporting electron injection and electron transport. The electron-transporting material can be selected from the electron-transporting materials for use in the ETL region as defined above.

The n-type dopant in the n-type doped EIL can be is selected from alkali metals, alkali metal compounds, alkaline earth metals, or alkaline earth metal compounds, or combinations thereof. The term "metal compounds" includes organometallic complexes, metal-organic salts, and inorganic salts, oxides and halides. Among the class of metal-containing n-type dopants, Li, Na, K, Rb, Cs, Mg, Ca, Sr, Ba, La, Ce, Sm, Eu, Tb, Dy, or Yb, and their compounds, are particularly useful. The materials used as the n-type dopants in the n-type doped EIL also include organic reducing agents with strong electron-donating properties. By "strong electron-donating properties" it is meant that the organic dopant should be able to donate at least some electronic charge to the host to form a charge-transfer complex with the host. Nonlimiting examples of organic molecules include bis(ethylenedithio)-tetrathiafulvalene (BEDT-TTF), tetrathiafulvalene (TTF), and their derivatives. In the case of polymeric hosts, the dopant is any of the above or also a material molecularly dispersed or copolymerized with the host as a minor component. Preferably, the n-type dopant in the n-type doped EIL includes Li, Na, K, Rb, Cs, Mg, Ca, Sr, Ba, La, Ce, Nd, Sm, Eu, Tb, Dy, or Yb, or combinations thereof. The n-type doped concentration is preferably in the range of 0.01-20% by volume of this layer.

The thickness of the EIL is typically less than 20 nm, and preferably in the range of 10 nm to 5 nm or less.

Cathode

When light emission is viewed solely through the anode, the cathode 140 includes nearly any conductive material. Desirable materials have effective film-forming properties to ensure effective contact with the underlying organic layer, promote electron injection at low voltage, and have effective stability. Useful cathode materials often contain a low work function metal (<4.0 eV) or metal alloy. One preferred cathode material includes a Mg:Ag alloy as described in U.S. Pat. No. 4,885,221. Another suitable class of cathode materials includes bilayers including a thin inorganic EIL in contact with an organic layer (e.g., organic EIL or ETL), which is capped with a thicker layer of a conductive metal. Here, the inorganic EIL preferably includes a low work function metal or metal salt and, if so, the thicker capping layer does not need to have a low work function. One such cathode includes a thin layer of LiF followed by a thicker layer of Al as described in U.S. Pat. No. 5,677,572. Other useful cathode material sets include, but are not limited to, those disclosed in U.S. Pat. Nos. 5,059,861; 5,059,862, and 6,140,763.

When light emission is viewed through the cathode, cathode 140 should be transparent or nearly transparent. For such applications, metals should be thin or one should use transparent conductive oxides, or include these materials. Optically transparent cathodes have been described in more detail in U.S. Pat. Nos. 4,885,211; 5,247,190; 5,703,436; 5,608,287; 5,837,391; 5,677,572; 5,776,622; 5,776,623; 5,714,838; 5,969,474; 5,739,545; 5,981,306; 6,137,223; 6,140,763; 6,172,459; 6,278,236; 6,284,393, and EP 1 076 368. Cathode materials are typically deposited by thermal evaporation, electron beam evaporation, ion sputtering, or chemical vapor deposition. When needed, patterning is achieved through many well known methods including, but not limited to, through-mask deposition, integral shadow masking, for example as described in U.S. Pat. No. 5,276,380 and EP 0 732 868, laser ablation, and selective chemical vapor deposition.

The thickness of the EIL is often in the range of from 0.1 nm to 20 nm, and typically in the range of from 1 nm to 5 nm.

Substrate

OLED 100 is typically provided over a supporting substrate 110 where either the anode 120 or cathode 140 can be in contact with the substrate. The electrode in contact with the substrate is conveniently referred to as the bottom electrode. Conventionally, the bottom electrode is the anode 120, but this invention is not limited to that configuration. The substrate can either be light transmissive or opaque, depending on the intended direction of light emission. The light transmissive property is desirable for viewing the EL emission through the substrate. Transparent glass or plastic is commonly employed in such cases. The substrate can be a complex structure comprising multiple layers of materials. This is typically the case for active matrix substrates wherein TFTs are provided below the OLED layers. It is still necessary that the substrate, at least in the emissive pixelated areas, include largely transparent materials such as glass or polymers. For applications where the EL emission is viewed through the top electrode, the transmissive characteristic of the bottom support is immaterial, and therefore the substrate can be light transmissive, light absorbing or light reflective. Substrates for use in this case include, but are not limited to, glass, plastic, semiconductor materials such as silicon, ceramics, and circuit board materials. Again, the substrate can be a complex structure including multiple layers of materials such as found in active matrix TFT designs. It is necessary to provide in these device configurations a light-transparent top electrode.

Deposition of Organic Layers

The organic materials mentioned above are suitably deposited through sublimation, but can be deposited from a solvent with an optional binder to improve film formation. If the material is a polymer, solvent deposition is usually preferred. The material to be deposited by sublimation can be vaporized from a sublimator "boat" often comprised of a tantalum material, e.g., as described in U.S. Pat. No. 6,237,529, or can be first coated onto a donor sheet and then sublimed in closer proximity to the substrate. Layers with a mixture of materials can utilize separate sublimator boats or the materials can be pre-mixed and coated from a single boat or donor sheet. Patterned deposition can be achieved using shadow masks, integral shadow masks (U.S. Pat. No. 5,294,870), spatially-defined thermal dye transfer from a donor sheet (U.S. Pat. Nos. 5,851,709 and 6,066,357) and inkjet method (U.S. Pat. No. 6,066,357).

Organic materials useful in making OLEDs, for example organic hole-transporting materials, organic light-emitting materials doped with an organic electroluminescent components have relatively complex molecular structures with relatively weak molecular bonding forces, so that care must be taken to avoid decomposition of the organic material(s) during physical vapor deposition. The aforementioned organic materials are synthesized to a relatively high degree of purity, and are provided in the form of powders, flakes, or granules. Such powders or flakes have been used heretofore for placement into a physical vapor deposition source wherein heat is applied for forming a vapor by sublimation or vaporization of the organic material, the vapor condensing on a substrate to provide an organic layer thereon.

Several problems have been observed in using organic powders, flakes, or granules in physical vapor deposition. These powders, flakes, or granules are difficult to handle. These organic materials generally have a relatively low physical density and undesirably low thermal conductivity, particularly when placed in a physical vapor deposition source which is disposed in a chamber evacuated to a reduced pressure as low as $10^{-6}$ Torr. Consequently, powder particles, flakes, or granules are heated only by radiative heating from a heated source, and by conductive heating of particles or flakes directly in contact with heated surfaces of the source. Powder particles, flakes, or granules which are not in contact with heated surfaces of the source are not effectively heated by conductive heating due to a relatively low particle-to-particle contact area; this can lead to nonuniform heating of such organic materials in physical vapor deposition sources. Therefore, this can result in potentially nonuniform vapor-deposited organic layers formed on a substrate.

These organic powders can be consolidated into a solid pellet. These solid pellets consolidating into a solid pellet from a mixture of a sublimable organic material powder are easier to handle. Consolidation of organic powder into a solid pellet can be accomplished with relatively simple tools. A solid pellet formed from mixture including one or more non-luminescent organic non-electroluminescent component materials or luminescent electroluminescent component materials or mixture of non-electroluminescent component and electroluminescent component materials can be placed into a physical vapor deposition source for making organic layer. Such consolidated pellets can be used in a physical vapor deposition apparatus.

In one aspect, the present invention provides a method of making an organic layer from compacted pellets of organic materials on a substrate, which will form part of an OLED.

One preferred method for depositing the materials of the present invention is described in U.S. Patent Application Publication No. 2004/0255857 and U.S. Pat. No. 7,288,286 where different source evaporators are used to evaporate each of the materials of the present invention. A second preferred method involves the use of flash evaporation where materials are metered along a material feed path in which the material feed path is temperature controlled. Such a preferred method is described in the following commonly assigned U.S. Pat. Nos. 7,232,588; 7,238,389; 7,288,285; 7,288,286; 7,165,340 and U.S. Patent Application Publication No. 2006/0177576. Using this second method, each material can be evaporated using different source evaporators or the solid materials can be mixed prior to evaporation using the same source evaporator.

Encapsulation

Most OLED devices are sensitive to moisture and oxygen so they are commonly sealed in an inert atmosphere such as nitrogen or argon, along with a desiccant such as alumina, bauxite, calcium sulfate, clays, silica gel, zeolites, alkaline metal oxides, alkaline earth metal oxides, sulfates, or metal halides and perchlorates. Methods for encapsulation and desiccation include, but are not limited to, those described in U.S. Pat. No. 6,226,890.

OLED Device Design Criteria

For full color display, the pixelation of LELs can be needed. This pixelated deposition of LELs is achieved using shadow masks, integral shadow masks, U.S. Pat. No. 5,294,870, spatially defined thermal dye transfer from a donor sheet, U.S. Pat. Nos. 5,688,551; 5,851,709, and 6,066,357, and inkjet method, U.S. Pat. No. 6,066,357.

OLEDs of this invention can employ various well-known optical effects in order to enhance their emissive properties if desired. This includes optimizing layer thicknesses to yield maximum light transmission, providing dielectric mirror structures, replacing reflective electrodes with light-absorbing electrodes, providing anti-glare or anti-reflection coatings over the display, providing a polarizing medium over the display, or providing colored, neutral density, or color-conversion filters over the display. Filters, polarizers, and anti-glare or anti-reflection coatings can be specifically provided over the OLED or as part of the OLED.

OLED devices of this invention can employ various well-known optical effects in order to enhance its properties if desired. This includes optimizing layer thicknesses to yield maximum light transmission, providing dielectric mirror structures, replacing reflective electrodes with light-absorbing electrodes, providing anti-glare or anti-reflection coatings over the display, providing a polarizing medium over the display, or providing colored, neutral density, or color-conversion filters over the display. Filters, polarizers, and anti-glare or anti-reflection coatings can be specifically provided over the cover or as part of the cover.

Embodiments of the invention can provide EL devices that have good luminance efficiency, good operational stability, and reduced drive voltages. Embodiments of the invention can also give reduced voltage rises over the lifetime of the devices and can be consistently produced with high reproducibility to provide good light efficiency. They can have lower power consumption requirements and, when used with a battery, provide longer battery lifetimes.

The invention and its advantages are further illustrated by the specific examples that follow. The term "percentage" or "percent" and the symbol "%" indicate the volume percent (or a thickness ratio as measured on a thin film thickness monitor) of a particular first or second compound of the total material in the layer of the invention and other components of the devices. If more than one second compound is present, the total volume of the second compounds can also be expressed as a percentage of the total material in the layer of the invention.

Example 1

Synthesis of Inventive Compound Inv-1

Inv-1 was synthesized as outlined in Scheme 1 and described below.

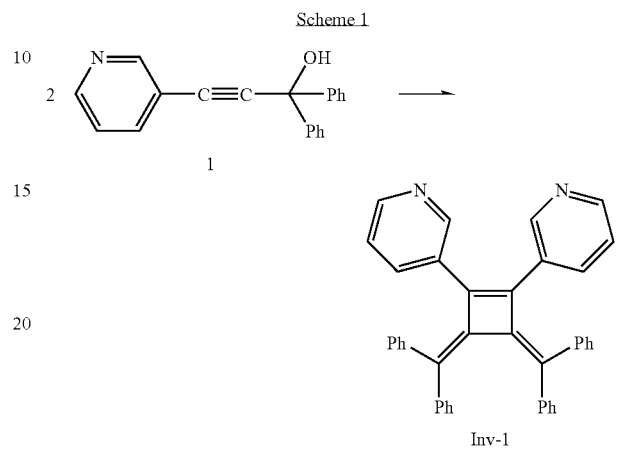

Figure 2:
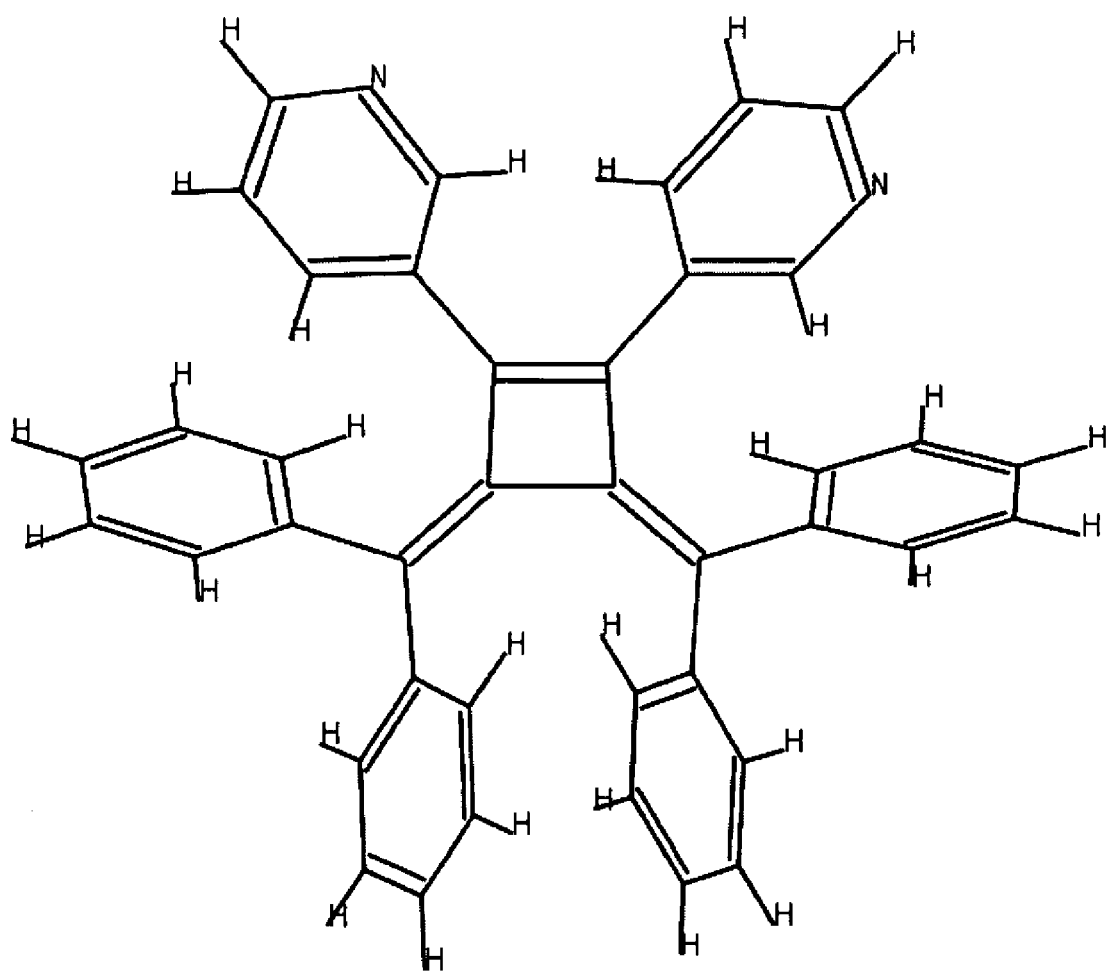
FIG. 2 shows a structure representation of cyclobutene Inv-1 obtained from X-ray analysis.

1,1-Diphenyl-3-(3-pyridyl)-2-propyn-1-ol(compound 1, 7.5 g, 26 mMole) was suspended in dichloromethane (50 mL) and tetrahydrofuran (30 mL), and the mixture was stirred under a nitrogen atmosphere and gently heated to achieve a solution. To this solution was then added triethylamine (5.11 mL, 36 mMole) and 4-dimethylaminopyridine (100 mg) and the solution was cooled to below 0° C. in an ice/acetone bath. Methanesulfonyl chloride (3.12 mL, 36 mMoles) was then added dropwise at such a rate as to maintain the temperature in the 0 to 5° C. range. After this addition, the temperature was allowed to fall to −5° C. and the reaction mixture was stirred at this temperature for 15 min. and then finally stirred for another 15 min. without the cooling bath. During this time, the temperature of the reaction mixture increased to room temperature. Toluene (100 mL) was then added together with finely powdered potassium carbonate (4.9 g, 35.5 mMole). The reaction flask was fitted with a Dean-Stark trap and gradually heated to collect the dichloromethane and tetrahydrofuran. During this heating period and as these volatile solvents were removed, they were gradually replaced with an equal volume of toluene. The resulting toluene solution was then heated at reflux for 8 hours. The solution was then cooled, diluted with ethyl acetate, washed with water (3×100 mL) and dried over magnesium sulfate. After removal of the magnesium sulfate by filtration, the solvent was distilled at reduced pressure, and the residue was treated with diethyl ether. The solid formed was collected, washed with diethyl ether, and then methanol, and air dried. This afforded 1.5 g of crude product which was sublimed at 205 to 210° C./3×10⁻¹ Torr to yield Inv-1 as yellow crystals. The structure of Inv-1 was confirmed by Field Desorption Mass Spectrometry, $[m+H]^+$: 537, and nmr spectroscopy. Further confirmation was obtained by single crystal X-ray analysis and a structure representation is shown in FIG. 2.

Example 2

Electrochemical Redox Potentials and Estimated Energy Levels

LUMO and HOMO values are typically estimated experimentally by electrochemical methods. The following method illustrates a useful way to measure redox properties. A Model CHI660 electrochemical analyzer (CH Instruments, Inc., Austin, Tex.) was employed to carry out the electrochemical measurements. Cyclic voltammetry (CV) and Osteryoung square-wave voltammetry (SWV) were used to characterize the redox properties of the compounds of interest. A glassy carbon (GC) disk electrode (A=0.071 cm$^2$) was used as working electrode. The GC electrode was polished with 0.05 μm alumina slurry, followed by sonication cleaning in Milli-Q deionized water twice and rinsed with acetone in between water cleaning. The electrode was finally cleaned and activated by electrochemical treatment prior to use. A platinum wire served as counter electrode and a saturated calomel electrode (SCE) was used as a quasi-reference electrode to complete a standard 3-electrode electrochemical cell. Ferrocene (Fc) was used as an internal standard ($E_{Fc}$=0.50 V vs. SCE in 1:1 acetonitrile/toluene, 0.1 M TBAF). A mixture of acetonitrile and toluene (50%/50% v/v, or 1:1) was used as the organic solvent system. The supporting electrolyte, tetrabutylammonium tetrafluoroborate (TBAF) was recrystallized twice in isopropanol and dried under vacuum. All solvents used were low water grade (<20 ppm water). The testing solution was purged with high purity nitrogen gas for approximately 5 minutes to remove oxygen and a nitrogen blanket was kept on the top of the solution during the course of the experiments. All measurements were performed at ambient temperature of 25±1° C. The oxidation and reduction potentials were determined either by averaging the anodic peak potential (Ep,a) and cathodic peak potential (Ep,c) for reversible or quasi-reversible electrode processes or on the basis of peak potentials (in SWV) for irreversible processes. LUMO and HOMO values are calculated from the following equations:

Formal reduction potentials vs. SCE for reversible or quasi-reversible processes;

$$E^{o\prime}_{red}=(E_{pa}+E_{pc})/2$$

$$E^{o\prime}_{ox}=(E_{pa}+E_{pc})/2$$

Formal reduction potentials vs. Fc;

$$E^{o\prime}_{red} \text{ vs. } Fc=(E^{o\prime}_{red} \text{ vs. } SCE)-E_{Fc}$$

$$E^{o\prime}_{ox} \text{ vs. } Fc=(E^{o\prime}_{ox} \text{ vs. } SCE)-E_{Fc}$$

where $E_{Fc}$ is the oxidation potential $E_{ox}$, of ferrocene; Estimated lower limit for LUMO and HOMO values;

$$LUMO=HOMO_{Fc}-(E^{o\prime}_{red} \text{ vs. } Fc)$$

$$HOMO=HOMO_{Fc}-(E^{o\prime}_{ox} \text{ vs. } Fc)$$

where $HOMO_{Fc}$ (Highest Occupied Molecular Orbital for ferrocene)=−4.8 eV.

Redox potentials as well as estimated HOMO and LUMO values are summarized in Table 1.

TABLE 1

Redox Potentials and Estimated Energy Levels.

| Compound | $E^{o\prime}$(ox) V vs. SCE | $E^{o\prime}$(red) V vs. SCE | $E^{o\prime}$(ox) V vs. FC | $E^{o\prime}$(red) V vs. FC | HOMO (eV) | LUMO (eV) |
|---|---|---|---|---|---|---|
| Inv-1 | 1.8 | −1.655 | >1.3 | −2.16 | <−6.1 | −2.65 |
| FA-1 | 1.67 | −1.67 | 1.17 | −2.19 | −5.97 | −2.61 |
| FA-2/ FA-3* | 1.67 | −1.64 | 1.17 | −2.14 | −5.97 | −2.66 |
| P-2 | 1.308 | −1.855 | 0.808 | −2.355 | −5.61 | −2.44 |
| P-4 | 1.345 | −1.847 | 0.845 | −2.347 | −5.64 | −2.45 |

*A 60/40 mixture of isomers FA-2 and FA-3

As can be seen from Table 1 the estimated LUMO energy values of fluoranthene derivatives FA-1 and FA-2/FA-3 mixture are very close (within 0.1 eV) of that of Inv-1. The anthracene derivatives P-2 and P-4 also have estimated LUMO values relatively close (0.2 eV) to that of Inv-1.

Example 3

Preparation of Blue-Light Emitting OLED Devices 3.1 through 3.12

A series of OLED devices (3.1 through 3.6) were constructed in the following manner:

1. A glass substrate coated with an 85 nm layer of indium-tin oxide (ITO), as the anode, was sequentially ultrasonicated in a commercial detergent, rinsed in deionized water and exposed to oxygen plasma for about 1 min.

2. Over the ITO was deposited a 1 nm fluorocarbon ($CF_x$) hole-injecting layer (HIL) by plasma-assisted deposition of $CHF_3$ as described in U.S. Pat. No. 6,208,075.

3. Next a layer of hole-transporting material 4,4'-Bis[N-(1-naphthyl)-N-phenylamino]biphenyl (NPB) was deposited to a thickness of 95 nm.

4. A 20 nm light-emitting layer (LEL) corresponding to the host material P-4 and 1.5% by volume of FD-54 was then deposited.

5. An electron-transporting layer (ETL) consisting of a mixture of isomeric compounds FA-2 and FA-3 (60/40 ratio) at a thickness as shown in Table 2 was vacuum-deposited over the LEL.

6. Except for device 3.1, a first electron-injecting layer (EIL1) corresponding to Inv-1 at a thickness shown in Table 2 was vacuum-deposited over the LEL.

7. A second electron-injecting layer (EIL2) corresponding to LiF at a thickness of was 0.5 nm was vacuum deposited onto the ETL1 layer. For device 3.1 this layer was deposited directly on the ETL.

8. And finally, a 100 nm layer of aluminum was deposited onto the EIL, to form the cathode.

The above sequence completes the deposition of the EL device. The device was then hermetically packaged in a dry glove box for protection against ambient environment.

A second set of devices (3.7 through 3.12) were prepared in the same manner as devices 3.1-3.6 except, Inv-1, when present, was replaced with C-1.

During preparation each device was duplicated to give four identically fabricated devices for each example. The devices formed were tested for drive voltage and luminous efficiency at an operating current of 20 mA/cm$^2$. The results of the four duplicate devices were averaged and the results are reported in Table 2.

C-1

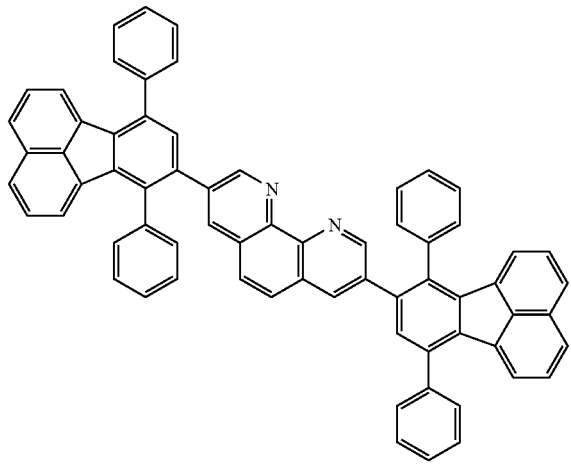

TABLE 2

Performance of Devices 3.1-3.12.

| Example (Type) | ETL (FA-2/FA-3) Level (nm) | EIL1 | EIL1 Level (nm) | Drive Volt. (Volts) | Efficiency (cd/A) |
|---|---|---|---|---|---|
| 3.1 (Comparative) | 35.0 | — | — | 10.1 | 1.6 |
| 3.2 (Inventive) | 34.0 | Inv-1 | 1.0 | 6.7 | 4.3 |
| 3.3 (Inventive) | 32.0 | Inv-1 | 2.0 | 5.0 | 6.1 |
| 3.4 (Inventive) | 30.0 | Inv-1 | 5.0 | 5.6 | 5.7 |
| 3.5 (Inventive) | 27.5 | Inv-1 | 7.5 | 9.5 | 2.0 |
| 3.6 (Inventive) | 25.0 | Inv-1 | 10.0 | 7.6 | 2.4 |
| 3.7 (Comparative) | 35.0 | — | — | 9.1 | 2.3 |
| 3.8 (Comparative) | 34.0 | C-1 | 1.0 | 6.3 | 5.0 |
| 3.9 (Comparative) | 33.0 | C-1 | 2.0 | 5.9 | 5.5 |
| 3.10 (Comparative) | 30.0 | C-1 | 5.0 | 8.2 | 2.8 |
| 3.11 (Comparative) | 27.5 | C-1 | 7.5 | 8.3 | 2.7 |
| 3.12 (Comparative) | 25.0 | C-1 | 10.0 | 7.6 | 2.9 |

As shown in Table 2, although the devices all have the same thickness, by including a layer of Inv-1 between the electron-transporting layer and the cathode (devices 3.2 through 3.6) one obtains devices with higher luminance and lower drive voltage relative to the comparative device 3.1, which does not contain Inv-1. In particular, devices 3.3 and 3.4 provide very high luminance efficiency and low drive voltage.

It can be appreciated that individual compounds when used in an EL device can have different optimum thickness levels. For Inv-1, in the format of Example 3, device 3.3 having a thickness of 2.0 nm provides the best luminance at the lowest drive voltage. Comparison compound C-1 (devices 3.8-3.12) also has optimum performance at 2.0 nm (device 3.9). By comparing the performance of device 3.2 and 3.9 it is clear that Inv-1 provides better luminance and lower drive voltage relative to C-1. Compound C-1 is similar in structure to materials described in U.S. Patent Application Publication No. 2006/0097227 and JP 2004091444.

Example 4

Preparation of Red-Light Emitting Devices 4.1 through 4.6

A series of OLED devices (4.1 through 4.6) were constructed in the following manner:

1. A glass substrate coated with an 85 nm layer of indium-tin oxide (ITO), as the anode, was sequentially ultrasonicated in a commercial detergent, rinsed in deionized water and exposed to oxygen plasma for about 1 min.

2. Over the ITO was deposited a 1 nm fluorocarbon ($CF_x$) hole-injecting layer (HIL) by plasma-assisted deposition of $CHF_3$ as described in U.S. Pat. No. 6,208,075.

3. Next a layer of hole-transporting material 4,4'-Bis[N-(1-naphthyl)-N-phenylamino]biphenyl (NPB) was deposited to a thickness of 144.0 nm.

4. A 40 nm light-emitting layer (LEL) corresponding to 64.5% by volume of a first host material, rubrene (FD-5), and 35.0% by volume of a second host material corresponding to an isomer mixture of FA-2 and FA-3 (60/40 ratio), and 0.5% by volume of dopant FD-46 was then deposited.

5. An electron-transporting layer (ETL) corresponding to an isomer mixture of FA-2 and FA-3 (60/40 ratio) at a thickness shown in Table 3 was vacuum-deposited over the LEL.

6. Except for device 4.1, a first electron-injecting layer (EIL1) corresponding to Inv-1 at a thickness shown in Table 3 was vacuum-deposited over the LEL.

7. A second electron-injecting layer (EIL2) corresponding to LiF at a thickness of 0.5 nm was vacuum deposited onto the ETL1 layer. For device 4.1 this layer was deposited directly on the ETL.

8. And finally, a 100 nm layer of aluminum was deposited onto the EIL, to form the cathode.

The above sequence completes the deposition of the EL device. The device was then hermetically packaged in a dry glove box for protection against ambient environment.

During their preparation each device was duplicated to give four identically fabricated devices for each example. The devices formed were tested for drive voltage and luminous efficiency at an operating current of 20 mA/cm². The results from the four duplicate devices were averaged and the results are reported in Table 3.

TABLE 3

Performance of Devices 4.1-4.6.

| Example (Type) | ETL (FA-2/FA-3) Level (nm) | EIL1 | EIL1 Level (nm) | Drive Volt. (Volts) | Efficiency (cd/A) |
|---|---|---|---|---|---|
| 4.1 (Comparative) | 35.0 | — | — | 5.9 | 5.2 |
| 4.2 (Inventive) | 34.0 | Inv-1 | 1.0 | 5.5 | 6.6 |
| 4.3 (Inventive) | 32.0 | Inv-1 | 2.0 | 5.4 | 7.2 |
| 4.4 (Inventive) | 30.0 | Inv-1 | 5.0 | 5.4 | 7.8 |
| 4.5 (Inventive) | 27.5 | Inv-1 | 7.5 | 5.4 | 7.4 |
| 4.6 (Inventive) | 25.0 | Inv-1 | 10.0 | 5.7 | 6.1 |

As shown in Table 3 that the inventive devices 4.2 through 4.6 provide higher luminance relative to comparative device 4.1, which does not contain Inv-1. In particular, devices 4.2 through 4.5 offer both higher luminance efficiency and lower drive voltage. All devices have the same thickness.

Example 5

Preparation of Blue-Light Emitting OLED Devices 5.1 through 5.6.

A series of OLED devices (5.1 through 5.6) were constructed in the following manner:

1. A glass substrate coated with an 85 nm layer of indium-tin oxide (ITO), as the anode, was sequentially ultrasonicated in a commercial detergent, rinsed in deionized water and exposed to oxygen plasma for about 1 min.

2. Over the ITO was deposited a 1 nm fluorocarbon ($CF_x$) hole-injecting layer (HIL) by plasma-assisted deposition of $CHF_3$ as described in U.S. Pat. No. 6,208,075.

3. Next a layer of hole-transporting material 4,4'-Bis[N-(1-naphthyl)-N-phenylamino]biphenyl (NPB) was deposited to a thickness of 95 nm.

4. A 20 nm light-emitting layer (LEL) corresponding to the host material P-4 and 1.5% by volume of FD-54 was then deposited.

5. An electron-transporting layer (ETL) consisting of P-4 at a thickness as shown in Table 4 was vacuum-deposited over the LEL.

6. Except for device 5.1, a first electron-injecting layer (EIL1) corresponding to Inv-1 at a thickness shown in Table 4 was vacuum-deposited over the LEL.

7. A second electron-injecting layer (EIL2) corresponding to LiF at a thickness of was 0.5 nm was vacuum deposited onto the ETL1 layer. For device 5.1 this layer was deposited directly on the ETL.

8. And finally, a 100 nm layer of aluminum was deposited onto the EIL, to form the cathode.

The above sequence completes the deposition of the EL device. The device was then hermetically packaged in a dry glove box for protection against ambient environment.

The devices formed were tested for drive voltage and luminous efficiency at an operating current of 20 mA/cm$^2$. The results are reported in Table 4.

TABLE 4

Performance of Devices 5.1-5.6.

| Example (Type) | ETL P-4 Level (nm) | EIL1 | EIL1 Level (nm) | Drive Volt. (Volts) | Efficiency (cd/A) |
|---|---|---|---|---|---|
| 5.1 (Comparative) | 35.0 | — | — | 12.0 | 0.08 |
| 5.2 (Inventive) | 34.0 | Inv-1 | 1.0 | 10.9 | 1.4 |
| 5.3 (Inventive) | 32.0 | Inv-1 | 2.0 | 9.4 | 2.2 |
| 5.4 (Inventive) | 30.0 | Inv-1 | 5.0 | 9.1 | 2.4 |
| 5.5 (Inventive) | 27.5 | Inv-1 | 7.5 | 9.5 | 1.9 |
| 5.6 (Inventive) | 25.0 | Inv-1 | 10.0 | 9.2 | 1.6 |

Devices 5.2-5.6 illustrate the use of an ETL containing anthracene P-4 in combination with an EIL1 containing Inv-1 and an EIL2 containing LiF. The inventive devices afforded lower voltage and higher luminance relative to the comparative device 5.1 that does not contain Inv-1, even though all devices have the same thickness.

The invention has been described in detail with particular reference to certain preferred embodiments thereof, but it will be understood that variations and modifications can be effected within the spirit and scope of the invention.

PARTS LIST

100 OLED
110 Substrate
120 Anode
130 Hole-Injecting layer (HIL)
132 Hole-Transporting layer (HTL)
134 Light-Emitting layer (LEL)
135 Hole-Blocking Layer (HBL)
136 Electron-Transporting layer (ETL)
138 Electron-Injecting layer (EIL)
140 Cathode
150 Voltage/Current Source
160 Electrical Connectors

The invention claimed is:

1. An OLED device comprising a cathode, an anode, and having therebetween a light-emitting layer and further comprising a first layer between the light-emitting layer and the cathode containing a cyclobutene compound comprising a cyclobutene nucleus substituted in the 1-position with a five- or six-membered heteroaromatic ring group containing at least one trivalent nitrogen atom; substituted in the 2-position with an aromatic ring group; and substituted with a first methylene group in the 3-position and a second methylene group in the 4-position, provided said first and second methylene groups are further disubstituted in the 1',1'-positions and the 1",1"-positions with independently selected aromatic groups.

2. The OLED device of claim 1 wherein the heteroaromatic ring group is an azine group.

3. The OLED device of claim 2 wherein the azine group is selected from the group consisting of a pyridine group, a pyrazine group, a pyrimidine group, and a phenanthroline group.

4. The OLED device of claim 1 wherein the aromatic ring group in the 2-position is a five- or six-membered heteroaromatic ring group containing at least one trivalent nitrogen atom.

5. The OLED device of claim 1 wherein the cyclobutene compound is represented by Formula (I),

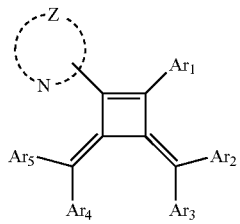

Formula (I)

wherein:
Z represents the atoms necessary to complete a five- or six-membered aromatic ring containing at least one trivalent nitrogen; and
$Ar_1$-$Ar_5$ each represents an independently chosen aryl group or heteroaryl group.

6. The OLED device of claim 5 wherein Z represents the atoms necessary to complete an azine ring group, $Ar_1$ represents a heteroaryl group, and each $Ar_2$-$Ar_5$ represents an independently chosen aryl group having 6-24 carbon atoms.

7. The OLED device of claim 5 wherein Z represents the atoms necessary to complete a pyridine ring group and wherein the pyridine ring group contains no more than two fused rings.

8. The OLED device of claim 1 wherein the cyclobutene compound is represented by Formula (II),

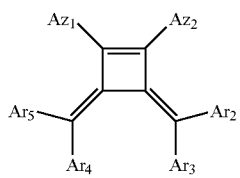

Formula (II)

wherein:
$Az_1$ and $Az_2$ each independently represent an azine group; and
$Ar_2$—$Ar_5$ each represents an independently chosen aryl group having 6-24 carbon atoms.

9. The OLED device of claim 8 wherein $Az_1$ and $Az_2$ are the same and each $Ar_2$-$Ar_5$ represents the same aryl groups having 6-24 carbon atoms.

10. The OLED device of claim 8 wherein $Az_1$ and $Az_2$ are selected from the group consisting of a pyridine group, a pyrazine ring group, a pyrimidine group, and a phenanthroline group.

11. The OLED device of claim 8 wherein $Az_1$ and $Az_2$ are the same and represent a pyridine ring group and wherein the pyridine ring group contains no more then two fused rings.

12. The OLED device of claim 8 wherein $Az_1$ and $Az_2$ are selected independently from the group consisting of:

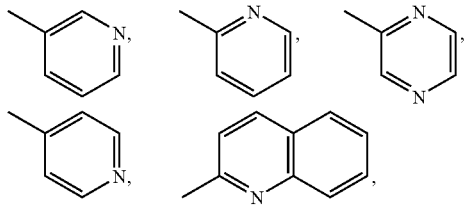

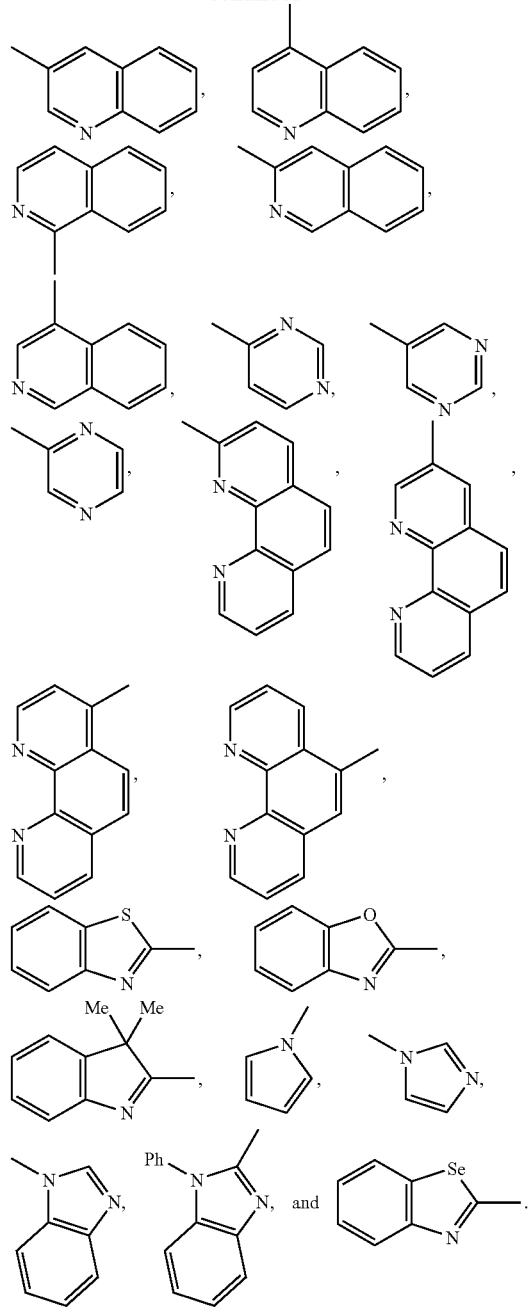

13. The OLED device of claim 1 wherein:
(a) the first layer includes an alkali metal or alkali metal compound; or
(b) wherein a second layer, located between said first layer and the cathode and contiguous to the first layer, contains an alkali metal or alkali metal compound; and
(c) provided that both the first and second layers can contain an independently selected alkali metal or alkali metal compound.

14. The OLED device of claim 13 wherein the alkali metal compound comprises LiF or an organic lithium compound represented by Formula (III):

$(Li^+)_m(Q)_n$      Formula (III)

wherein:
   Q is an anionic organic ligand; and
   m and n are independently selected integers selected to provide a neutral charge on the complex.

15. The OLED device of claim 1 wherein:
   (a) the first layer includes, in addition to the cyclobutene compound, a polycyclic aromatic hydrocarbon compound; or
   (b) a third layer, located between said first layer and the light-emitting layer and contiguous to the first layer, includes the polycyclic aromatic hydrocarbon compound, provided that both the first and third layers can include an independently selected polycyclic aromatic hydrocarbon compound; and wherein,
   (c) the polycyclic aromatic hydrocarbon compound comprises at least 3 fused aromatic rings and wherein the absolute difference in LUMO values between the polycyclic aromatic hydrocarbon compound and the cyclobutene compound is 0.3 eV or less.

16. The OLED device of claim 15 wherein the third layer includes an alkali metal or alkali metal compound.

17. The OLED device of claim 15 wherein the polycyclic aromatic hydrocarbon compound comprises an anthracene derivative of Formula (IV),

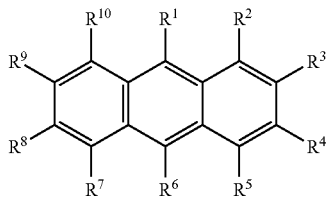

Formula (IV)

wherein:
   $R^1$ and $R^6$ each independently represent an aryl group having 6-24 carbon atoms;
   $R^2$-$R^5$ and $R^7$-$R^{10}$ are each independently chosen from hydrogen, alkyl groups having from 1-24 carbon atoms, and aryl groups having from 6-24 carbon atoms.

18. The OLED device of claim 15 wherein the polycyclic aromatic hydrocarbon compound comprises a fluoranthene derivative of Formula (V),

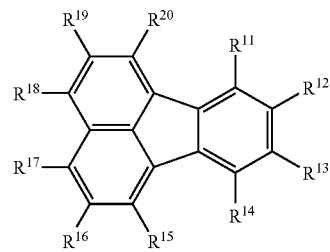

Formula (V)

wherein:
   $R^{11}$-$R^{20}$ are independently chosen from hydrogen, alkyl groups having from 1-24 carbon atoms, and aromatic groups having from 6-24 carbon atoms, provided adjacent groups can combine to form fused aromatic rings.

19. The OLED device of claim 18 wherein $R^{11}$ and $R^{14}$ represent aryl groups having 6-24 carbon atoms, and $R^{12}$, $R^{13}$ and $R^{15}$-$R^{20}$ are independently chosen from hydrogen, alkyl groups having from 1-24 carbon atoms, and aryl groups having from 6-24 carbon atoms, provided adjacent groups cannot combine to form fused aromatic rings.

20. A cyclobutene compound represented by Formula (VI):

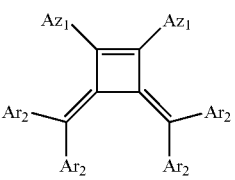

Formula (VI)

wherein:
   $Az_1$ represents an azine group; and
   $Ar_2$ represents an aryl group having 6-24 carbon atoms.

* * * * *